(12) United States Patent
Pei et al.

(10) Patent No.: US 9,209,405 B2
(45) Date of Patent: Dec. 8, 2015

(54) COMPOUND WITH BRANCHING ALKYL CHAINS, METHOD FOR PREPARING THE SAME, AND USE THEREOF IN PHOTOELECTRIC DEVICE

(71) Applicants: PEKING UNIVERSITY, Beijing (CN); BOE TECHNOLOGY GROUP CO., LTD., Beijing (CN)

(72) Inventors: Jian Pei, Beijing (CN); Ting Lei, Beijing (CN); Jinhu Dou, Beijing (CN)

(73) Assignees: PEKING UNIVERSITY, Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 27 days.

(21) Appl. No.: 13/935,779

(22) Filed: Jul. 5, 2013

(65) Prior Publication Data

US 2014/0011973 A1    Jan. 9, 2014

(30) Foreign Application Priority Data

Jul. 5, 2012 (CN) .......................... 2012 1 0232860

(51) Int. Cl.
| | |
|---|---|
| *C08G 73/06* | (2006.01) |
| *H01L 51/00* | (2006.01) |
| *C07D 417/14* | (2006.01) |
| *C07D 207/34* | (2006.01) |
| *C07D 209/34* | (2006.01) |

(52) U.S. Cl.
CPC .......... *H01L 51/0036* (2013.01); *C07D 207/34* (2013.01); *C07D 209/34* (2013.01); *C07D 417/14* (2013.01)

(58) Field of Classification Search
CPC .................................................. C08G 73/06
USPC ............ 528/243; 526/241; 568/840, 875, 876
See application file for complete search history.

(56) References Cited

U.S. PATENT DOCUMENTS

2010/0048672 A1    2/2010    Neuberg et al.

FOREIGN PATENT DOCUMENTS

| CN | 1743408 A | 3/2006 |
|---|---|---|
| CN | 101631553 A | 1/2010 |

OTHER PUBLICATIONS

Song Guo, et al; "Room-Temperature Long-Lived Triplet Excited States of Naphthalenediimides and Their Applications as Organic Triplet Photosensitizers for Photooxidation and Triplet-Triplet Annihilation Upconversions", The Journal of Organic Chemistry, vol. 77, pp. 3933-3943; Published Mar. 22, 2012.

(Continued)

*Primary Examiner* — Duc Truong
(74) *Attorney, Agent, or Firm* — Ladas & Parry LLP

(57) ABSTRACT

The invention discloses a compound having branching alkyl chains, the method for preparing the same and use thereof in photoelectric devices. By applying the branching alkyl chains as the solubilizing group to the preparation of organic conjugated molecules (for example, organic conjugated polymers), the number of methylenes between the resultant alky side chains and the backbone, i.e., m>1, which can effectively reduce the effect of the alkyl chains on the backbone π-π stacking, thereby ensuring the solubility of the organic conjugated molecule while greatly increasing the mobility of their carriers. It is suitable for an organic semiconductor material in photoelectric devices such as organic solar cells, organic light emitting diodes and organic field effect transistors, etc.

4 Claims, 1 Drawing Sheet

(56) References Cited

OTHER PUBLICATIONS

Mannepalli Lakshmi Kantam, et al; "Chemoselective Hydrogenation of the Olefinic Bonds Using a Palladium/Magnesium-Lanthanum Mixed Oxide Catalyst", Adv. Synth. Catal. vol. 354, pp. 663-669; Published online Feb. 23, 2012.

Extended European Search Report dated Jan. 20, 2014; EP13175244.

Second Chinese Office Action dated Feb. 24, 2014; Appln. No. 20120232860.9.

Pierre M. Beaujuge, et al; "Molecular Design and Ordering Effects in π-Functional Materials for Transistor and Solar Cell Applications", Journal of The American Chemical Society, vol. 133, pp. 20009-20029; Published Oct. 14, 2011.

Hugo Bronstein, et al; "Thieno[3,2-b]thiophene-Diketopyrrolopyrrole-Containing Polymers for High-Performance Organic Field-Effect Transistors and Organic Photovoltaic Devices", Journal of The American Chemical Society, vol. 133, pp. 3272-3275; Published Feb. 18, 2011.

Zhihua Chen, et al; "Naphthalenedicarboximide-vs Perylenedicarboximide-Based Copolymers, Synthesis and Semiconducting Properties in Bottom-Gate N-Channel Organic Transistors", Journal of The American Chemcial Society, vol. 131, pp. 8-9 Published on Web Dec. 17, 2008.

Junwu Chen, et al; "Development of Novel Conjugated Donor Polymers for High-Efficiency Bulk-Heterojunction Photovoltaic Devices", Accounts of Chemical Research, vol. 42, No. 11, Nov. 2009, pp. 1709-1718.

Chong-An Di, et al; "Interface Engineering: An Effective Approach toward High-Performance Organic Field-Effect Transistors", Accounts of Chemical Research, vol. 42, No. 10, Oct. 2009, pp. 1573-1583.

Jae Seun Ha, et al; "2,5-Bis(2-octyldodecyl)pyrrolo[3,4-c]pyrrole-1,4-(2H,5H)-dione-Based Donor-Acceptor Alternating Copolymer Bearing 5,5'-Di(thiophen-2-yl)-2,2'-biselenophene Exhibiting 1.5 cm2.v-1 Hole Mobility in Thin-Film Transistors", Journal of The American Chemcial Society, vol. 133, pp. 10364-10367, Published Jun. 17, 2011.

Zhicai He, et al; "Simultaneous Enhancement of Open-Circuit Voltage, Short-Circuit Current Density, and Fill Factor in Polymer Solar Cells", Advanced Materials, vol. 23, pp. 4636-4643; Article first published online: Sep. 9, 2011.

Alan R. Katritzky, et al; "Synthesis of Branched Long Chain Aliphatic Primary Alkyl Bromides", Organic Preparations and Procedures International: The New Journal for Organic Synthesis, vol. 21, Issue 2, pp. 129-133, Jan. 1989; Published online Feb. 18, 2009.

Ting Lei, et al; "High-Performance Air-Stable Organic Field-Effect Transistors: Isoindigo-Based Conjugated Polymers", Journal of The American Chemical Society, vol. 133, pp. 6099-6101, Published Apr. 5, 2011.

Ting Lei, et al; "Systematic Investigation of Isoindigo-Based Polymeric Filed-Effect Transistors: Design Strategy and Impact of Polymer Symmetry and Backbone Curvature", Chemistyr of Materials, vol. 24, pp. 1762-1770, Published May 2, 2012.

Joseph A. Letizia; et al; "High Electron Mobility in Solution-Cast and Vapor-Deposited Phenacyl-Quaterthiohene-Based Field-Effect Transistors: Toward N-Type Polythiophenes", Journal of The American Chemical Society, vol. 127, pp. 13476-13477, Published on Web Sep. 3, 2005.

Yuning Li, et al; "A High Mobility P-Type DPP-Thieno[3,2-b]thiophene Copolymer for Organic Thin-Film Transistors", Advanced Materials, vol. 22, pp. 4862-4866, Article first published online: Aug. 20, 2010.

Yongfang Li; "Molecular Design of Photovoltaic Materials for Polymer Solar Cells: Toward Suitable Electronic Energy Levels and Broad Absorption", Accounts of Chemical Research, vol. 45, No. 5, pp. 723-733, published on the Web Jan. 30, 2012.

Yongye Liang, et al; "For the Bright Future—Bulk Heterojunction Polymer Solar Cells with Power Conversion Efficiency of 7.4%", Advanced Energy Materials, vol. 22, pp. E135-E138, Article first published on line Jan. 4, 2010.

Peet, et al; "Efficiency enhancement in low-bandgap polymer solar cells by processing with alkane dithiols", Nature Materials, vol. 6, pp. 497-500; Published online May 27, 2007.

Jeffrey Peet, et al; ""Plastic" Solar Cells: Self-Assembly of Bulk Heterojunction Nanomaterials by Spontaneous Phase Separation", Accounts of Chemical Research, vol. 42, No. 11, pp. 1700-1708; Published on the Web Jul. 1, 2009.

N. Polgar, et al; Long-chain Acids containing a Quaternary Carbon Atom. Part II, Published on Jan. 1, 1943. Downloaded by State Intellectual Property Office of P.R.C. on Nov. 11, 2013; pp. 615-619.

H. Sirringhaus, et al; "Two-dimensional charge transport in self-organized, high-mobility conjugated polymers", Nature, vol. 401, Oct. 14, 1999, pp. 685-688.

Chengliang Wang, et al; "Semiconducting π-Conjugated Systems in Field-Effect Transistors: A Material Odyssey of Organic Electronics", Chemical Reviews, vol. 112, pp. 2208-2267, Published Nov. 23, 2011.

Yugen Wen, et al; "Recent Progress in n-Channel Thin-Film Transistors", Advanced Materials, vol. 22, pp. 1331-1345, Article first published online Jan. 14, 2010.

Xiaowei Zhan, et al; "A High-Mobility Electron-Transport Polymer with Broad Absorption and Its Use in Field-Effect Transistors and All-Polymer Solar Cells", Journal of The American Chemcial Society, vol. 129, pp. 7246-7247; Published on Web May 18, 2007.

First Chinese Office Action dated Dec. 2, 2013; Appln. No. 201210232860.9.

Zhihua Chen, et al; "Naphthalenedicarboximide-vs Perylenedicarboximide-Based Copolymers. Synthesis and Semiconducting Properties in Bottom-Gate N Channel Organic Transistors", Journal American Chemical Society, Jan. 14, 2009; 131(1):8-9.

Korean Examination Opinion dated Jan. 26, 2015; Appln. No. 10-2013-0078842.

Korean Examination Opinion dated May 20, 2015; Appln. No. 10-2013-0078842.

COMPOUND WITH BRANCHING ALKYL CHAINS, METHOD FOR PREPARING THE SAME, AND USE THEREOF IN PHOTOELECTRIC DEVICE

TECHNICAL FIELD

The invention relates to a compound with novel branching alkyl chains and a method for preparing the same, in particularly, relates to a class of organic electronic material with branching alkyl chains and a method for preparing the same. The invention belongs to the field of organic functional material and the field of organic electronics.

BACKGROUND

The structure of an organic conjugated molecule comprises a conjugated system consisting of delocalized π electrons, thereby presenting special optical, electric and magnetic properties, etc. which catches a wide attention of scientists and has become the focus of studies of the last 20 years. Synthesis based on organic conjugated molecules and functionalization and instrumentalization studies involve many kinds of disciplines such as chemistry, physics, electronics, material sciences, etc. They are multidisciplinary frontiers, filled with vigor and opportunities, and are among one of the important directions of future development of chemistry.

Due to their characteristics of lightness, thinness and flexibility, readiness for modification, etc., organic conjugated molecules have broad prospects of application in the field of photoelectric material. A series of remarkable results have already been obtained, especially in the fields of organic solar cell (OPV), organic light emitting diode (OLED) and organic field effect transistor (OFET), etc. Furthermore, since the organic field effect transistors have the characteristics of readiness for processing, low cost, capacity of large scale flexible preparation, readiness for integration, etc., present obvious advantages in studies in the fields of electronic paper, electronic label, active matrix addressing, sensor and storage, etc., and are considered as having great market potentials.

The organic field effect transistor is an active device regulating the electric circuit in an organic semiconductor by electric field. Its major device structure comprises the 4 following classes: (1) bottom gate bottom contact (BG/BC); (2) top gate bottom contact (TG/BC); (3) bottom gate top contact (BG/TC); and (4) top gate top contact (TG/TC) (Di, C. A.; Liu, Y. Q.; Yu, G.; Zhu, D. B. Acc. Chem. Res., 2009, 42, 1573). The organic field effect transistor consists essentially of electrodes, a dielectric layer, and an organic semiconductor layer, etc. It is essentially a capacitor carrying mobile charges. By applying a voltage between the gate electrode and the source electrode/drain electrode, charges will be induced at the interface between the semiconductor layer and the dielectric layer. When a small voltage is applied between the two electrodes, i.e., the source electrode and the drain electrode, an electric current is formed in the channel. Therefore, the magnitude of the induced charge at the interface can be controlled by adjusting the magnitude of the gate electrode voltage to achieve the on/off of the device, and the amplification of the signal is achieved by controlling the magnitude of the electric current by the voltage between the source electrode and the drain electrode.

The core of the organic field effect transistor is the organic semiconductor layer. The organic semiconductor layer can be classified into p type materials (transporting holes) and n type materials (transporting electrons) based on the difference of the carrier transported in the material; and it can also be classified into organic small molecular materials and organic conjugated polymer materials based on the difference of the type of the organic conjugated molecules. The organic conjugated polymer has been highly regarded because it enables the preparation of the device at a large scale with low cost by solution processing.

The studies on the p type polymer semiconductor materials were initially concentrated on polythiophene systems. The mobility of a sterically regular poly(3-hexylthiophene) (P3HT) can reach 0.05-0.2 $cm^2V^{-1}s^{-1}$ (Sirringhaus, H.; Brown, P. J.; Friend, R. H.; Nielsen, M. M.; Bechgaard, K.; Langeveld-Voss, B. M. W.; Spiering, A. J. H.; Janssen, R. A. J.; Meijer, E. W.; Herwig. P.; de Leeuw, D. M. Nature, 1999, 401, 685). Thereafter, more molecular construction units entered the radar screen of the researchers. These new structures conferred new vigor into this research area. For example, a mobility of 0.94 $cm^2V^{-1}s^{-1}$ was obtained for an organic conjugated polymer based on diketo-pyrrolo-pyrrole (DPP) in 2010 (Li, Y.; Singh, S. P.; Sonar, P. Adv. Mater., 2010, 22, 4862). In 2011, Bronstein reported that a mobility up to 1.94 $cm^2V^{-1}s^{-1}$ was obtained for a DPP-based polymer by different way of connection of the same construction blocks (Bronstein, H.; Chen, Z.; Ashraf, R. S.; Zhang, W.; Du, J.; Durrant, J. R.; Tuladhar, P. S.; Song, K.; Watkins, S. E.; Geerts, Y.; Wienk, M. M.; Janssen, R. A. J.; Anthopoulos, T.; Sirringhaus, H.; Heeney, M.; McCulloch, I. J. Am. Chem. Soc. 2011, 133, 3272). A compound obtained by the copolymerization of DPP and thiophene presented a mobility of 0.97 $cm^2V^{-1}s^{-1}$. By a structural modification that used biselenophene to replace bithiophene, a mobility of up to 1.5 $cm^2V^{-1}s^{-1}$ was obtained (Ha, J. S., Kim, K. H., Choi, D. H. J. Am. Chem. Soc. 2011, 133, 10364). Isoindigo type molecules are a family of molecules of significance in addition to DPP. In 2011, we reported that a mobility of 0.79 $cm^2V^{-1}s^{-1}$ and a device stability under high humidity up to 3 months were obtained for a polymer based on isoindigo structures (Lei, T.; Cao, Y.; Fan, Y.; Liu, C. J.; Yuan, S. C.; Pei, J. J. Am. Chem. Soc. 2011, 133, 6099).

In contrast, the development of n type polymer semiconductors is relatively slow. Among them, Facchetti and Marks reported that an electron mobility of 0.01 $cm^2V^{-1}s^{-1}$ was obtained for a polymer based on thiophene and fluorobenzene (Letizia, J. A.; Facchetti, A.; Stern, C. L.; Ratner, M. A.; Marks, T. J. J. Am. Chem. Soc. 2005, 127, 13476). Zhan et al. reported that a copolymer based on perylene diimide and dithienothiophene exhibited a good field effect performance and its electron mobility can reach 0.013 $cm^2V^{-1}s^{-1}$ (Zhan, X.; Tan, Z.; Domercq, B.; An, Z.; Zhang, X.; Barlow, S.; Li. Y.; Zhu, D.; Kippelen, B.; Marder, S. R. J. Am. Chem. Soc. 2007, 129, 7246). Moreover, a naphthalenedicarboximide based polymer reported by Facchetti in 2009 exhibited an electron mobility up to 0.85 $cm^2V^{-1}s^{-1}$ (Chen, Z.; Zheng, Y.; Yan, H.; Facchetti, A. J. Am. Chem. Soc. 2009, 131, 8).

Compared to the traditional silicon solar cells, the organic solar cells have the advantages of low cost, light weight, simple processing, readiness for large scale preparation and readiness for preparing flexible devices, etc. The structure of a device of an organic heterojunction solar cell is primarily classified into two types: one is the forward cell and the other is the reverse cell. The forward cell consists of an anode (generally ITO glass), a hole transport layer (generally PEDOT:PSS), active layer (composed of organic molecular such as organic conjugated polymers and fullerene derivatives, etc.), an electron transport layer, and a cathode (such as aluminum electrode). The reverse cell consists of a cathode (generally ITO glass), an electron transport layer (generally oxide semiconductors such as zinc oxide, etc.), an active layer (composed of organic molecular such as organic conjugated polymers and fullerene derivatives, etc.), an electron transport layer (generally semiconductors such as molybdenum trioxide, etc.), and an anode (such as silver electrode). The active layer is obtained by blending the two materials, i.e., the donor and the acceptor, and solution processing or evaporation them, in which the organic conjugated polymer can serve as both the donor and the acceptor. In an ideal bulk heterojunction structure, the donor and the acceptor form an alternating co-continuous phase, which results in a microphase separation at a scale of tens of nanometers which not only can separate the excitons generated by optical excitation with high efficiency, but also can effectively transport the carriers after the exciton separation to the electrodes to generate the electric current (J. Peet, A. J. Heeger, G. C. Bazan, Acc. Chem. Res. 2009, 42, 1700).

In recent years, studies on the organic bulk heterojunction solar cells based on the solution processing of polymers have achieved remarkable results. In 2007, Prof Heeger et al. increased the power conversion efficiency of PCDTBT from 2.8% to 5.5% by controlling the morphology of the active layer with additives (J. Peet, J. Y. Kim, N. E. Coates, W. L. Ma, D. Moses, A. J. Heeger, G. C. Bazan, Nat. Mater. 2007, 6, 497), and in the same year, a laminated device was prepared which obtained an power conversion efficiency of 6.5% (J. Y. Kim, K. Lee, N. E. Coates, D. Moses, T-Q Nguyen, M. Dante, A. L. Heeger, Science 2007, 317, 222). Yu group of University of Chicago and Yang group of University of California at Los Angeles reported a series of polymers based on thienothiophene and benzodithiophene structures and results of more than 5% power conversion efficiency were obtained (Y. Liang, L. Yu, Acc. Chem. Res. 2010, 43, 1227). Moreover, for the first time a polymer bulk heterojuction solar cell with a power conversion efficiency of more than 7% was reported, in which PTB7 achieved a power conversion efficiency up to 7.4% (Y. Liang, Z. Xu, J. Xia, S-T. Tsai, Y. Wu, G. Li, C. Ray, L, Yu, Adv. Mater. 2010, 22, E135). Cao group increased the power conversion efficiency of PECz-DTQx from 4% to 6.07% using PFN modified electrodes, and recently increased the efficiency of a bulk heterojunction solar cell with an inverted structure to 8.37% which passed the certification by National Center of Supervision and Inspection on Solar Photovoltatic Products Quality (Z. He, C. Zhang, X. Huang, W-Y. Wong, H. Wu, L. Chen, S. Su, Y. Cao, Adv. Mater. 2011, 23, 4636), and achieved the best results reported by current publications. Studies show that the efficiency of solar cells has close correlation to the mobility rate of polymers. Generally, the higher the mobility of the polymer, the higher of the efficiency of the solar cell (Chen, J.; Cao, Y. Acc. Chem. Res., 2009, 42, 1709). Therefore, increasing the mobility of the polymer has great significance on the studies on solar cells.

Organic conjugated polymers are a class of polymers obtained by polymerization of covalent bonds through conjugation from aromatic compounds. In order to ensure their good solubility and solution manufacturability, at least one solubilizing group needs to be introduced into at least one aromatic structure to increase their solubility. For example, the organic conjugated polymer as shown in the following formula:

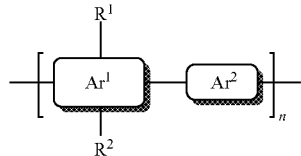

wherein $Ar^1$ and $Ar^2$ are fragments of aromatic compounds, respectively; $R^1$ and $R^2$ are solubilizing groups introduced into the aromatic core $Ar^1$, generally a group such as alkyl, halogen substituted alkyl, alkoxy, halogen substituted alkoxy, alkenyl, alkynyl, etc.; and n is the number of the repeating unit of the polymer, i.e., polymerization degree.

In primary studies (Lei, T.; Cao, Y; Zhou, X.; Peng, Y; Bian, J.; Pei, J. Chem. Mater 2012, 24, 1762.), we found that if a solubilizing group (such as an alkyl chain) is distributed in every one of the polymer units (as shown in FIG. 1(a)), it will affect the π-π stacking of the polymerization, thereby greatly affecting the mobility of the carriers in the polymer. This is because the van der Waals' radius between alkyl chains is 3.6-3.8 Å, while the distance of the π-π interaction is 3.4 Å (see the circle in FIG. 1(a) which indicates the repulsive effect of the alkyl chain against the aromatic group). As to this, we moved this alkyl chain from the smaller aromatic core $Ar^2$ to the larger aromatic core $Ar^1$, thereby increasing the mobility. On the other hand, traditionally a 2-branching alkyl chain (obtainable from Guerbet alcohol) is used as the solubilizing group (such as FIG. 1(b)) to avoid affecting the π-π stacking so as to achieve high mobility (Li, Y. Acc. Chem. Res., 2012, 45, 723; Wang, C.; Dong, H.; Hu, W.; Liu, Y.; Zhu, D. Chem. Rev., 2012, 112, 2208; Beaujuge, P. M.; Fréchet J. M. J. J. Am. Chem. Soc. 2011, 133, 20009; Wen, Y. Liu, Y. Adv. Mater 2010, 22, 1331; Chen, J.; Cao, Y. Acc. Chem. Res., 2009, 42, 1709). The purpose of the design is to ensure the π-π stacking while ensuring the solubility of the polymer.

SUMMARY

In view of the research efforts of the current polymer field effect transistor material and the low mobility of the polymers in the solar cell material researches, the object of the application is to provide compounds containing a type of novel branching alkyl chains, and apply them to the preparation of organic conjugated molecules, especially organic conjugated polymers. This novel branching alkyl chain ensures the solubility of the polymer while greatly increasing the mobility of the polymer material. This result has great significance on the polymer field effect transistor. Meanwhile, this result can also be used for small molecular field effect transistor materials and not limited to polymer field effect transistors. Because of the important status of the mobility of carriers in organic electronics, compounds and polymers containing these novel branching alkyl chains can also be applied to organic solar cell materials, organic light emitting diode materials, and organic field effect transistor materials, etc.

In the first aspect of the invention, a compound containing a branching alkyl chain having the general formula as shown in the following Formula (I) is provided:

Formula (I)

The aforementioned structure is different from a Guerbet alcohol (m=1). In the structure of Formula (I), m is an integer more than 1; R can be various substituents, such as halogen atoms (F, Cl, Br, I), hydroxyl, amino, trifluoromethanesulfonate group (MsO), p-toluenesulfonate group (TsO), azide group ($N_3$), cyano, alkenyl, alkynyl, alkoxy, etc.; $R^3$ and $R^4$ are the same or different, independently selected from alkyl, halogen substituted alkyl, alkoxy, halogen substituted alkoxy, alkenyl and alkynyl; $R^5$ is hydrogen, hydroxyl, alkyl, halogen substituted alkyl, alkoxy, halogen substituted alkoxy, alkenyl or alkynyl.

In Formula (I), m can, for example, be an integer of 2~18, an integer of 2~10, an integer of 3~18, an integer of 3~10, an integer of 3~5, or an integer of 3~4.

As a substituent of R, the alkenyl can, for example, be C2-C6 alkenyl, C2-C4 alkenyl, or ethenyl.

As a substituent of R, the alkynyl can, for example, be C2-C6 alkynyl, C2-C4 alkynyl, or ethynyl.

As a substituent of R, the alkoxy can, for example, be C1-C36 linear or branching alkoxy, or C1-C18 linear or branching alkoxy.

As a substituent of $R^3$, $R^4$ and $R^5$, the alkyl can, for example, be C1-C36 linear or branching alkyl, or C1-C18 linear or branching alkyl.

As a substituent of $R^3$, $R^4$ and $R^5$, the halogen substituted alkyl can, for example, be C1-C36 linear or branching halogen substituted alkyl, or C1-C18 linear or branching halogen substituted alkyl.

As a substituent of $R^3$, $R^4$ and $R^5$, the alkoxy can for example, be C1-C36 linear or branching alkoxy, or C1-C18 linear or branching alkoxy.

As a substituent of $R^3$, $R^4$ and $R^5$, the halogen substituted alkoxy can, for example, be C1-C36 linear or branching halogen substituted alkoxy, or C1-C18 linear or branching halogen substituted alkoxy.

As a substituent of $R^3$, $R^4$ and $R^5$, the alkenyl can, for example, be C2-C18 alkenyl, C2-C10 alkenyl, or C2-C6 alkenyl.

As a substituent of $R^3$, $R^4$ and $R^5$, the alkynyl can, for example, be C2-C18 alkynyl, C2-C10 alkynyl, or C2-C6 alkynyl.

Several specific examples of the aforementioned branching alkyl chains are given below.

When R is hydroxyl, m=2, $R^3$ and $R^4$ are 10 carbon-atom alkyls, $R^5$ is a hydrogen atom, the specific structure is as follows:

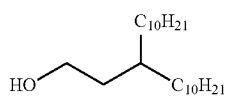

When R is halogen atom (such as I), m=2, $R^3$ and $R^4$ are 10 carbon-atom alkyls, $R^5$ is a hydrogen atom, the specific structure is as follows:

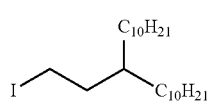

When R is hydroxyl, m=3, $R^3$ and $R^4$ are 14 carbon-atom alkyls, $R^5$ is a hydrogen atom, the specific structure is as follows:

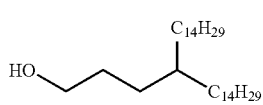

When R is hydroxyl, m=3, $R^3$ and $R^4$ are 18 carbon-atom alkyls, $R^5$ is a hydrogen atom, the specific structure is as follows:

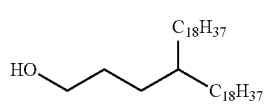

When R is amino, m=2, $R^3$ and $R^4$ are 10 carbon-atom alkyls, $R^5$ is a hydrogen atom, the specific structure is as follows:

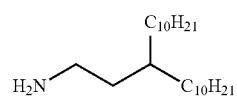

The procedure for preparing the compounds containing branching alkyl chains as shown in Formula (I) is as follows:

(1) Starting from the diol as shown in Formula (a), protection by a protecting group (sometimes is abbreviated as PG) is conducted:

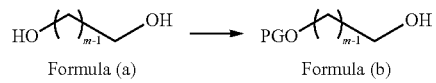

In this step, the protecting group can be selected from benzyl (Bn), various silicon protecting groups (such as trimethylsilyl (TMS), triethylsilyl (TES), triisopropylsilyl (TIPS), t-butyldimethylsilyl (TBDMS), t-butyldiphenylsilyl (TBDPS), etc.), methoxymethyl protecting group (MOM), tetrahydropyran protecting group (THP), p-methoxyphenyl protecting group (PMB), etc., and the reaction is as follows:

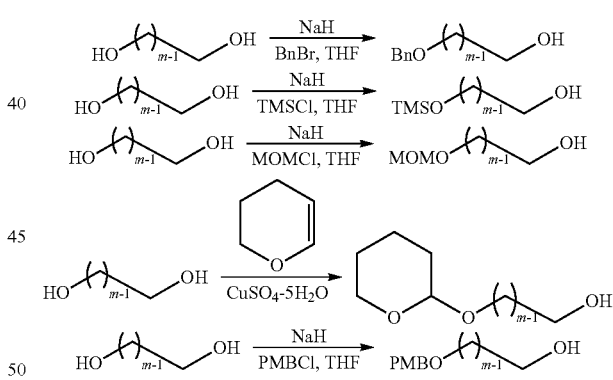

(2) The diol with one terminus protected (Formula (b) compound) is oxidized to obtain the carboxylic acid as shown in Formula (c). This oxidation can be selected from various reactions that oxidize alcohols to carboxylic acids, such as Jones oxidation ($CrO_3$—$H_2SO_4$) reaction, or performing oxidation step by step (first oxidized into an aldehyde and then oxidized into a carboxylic acid), etc.

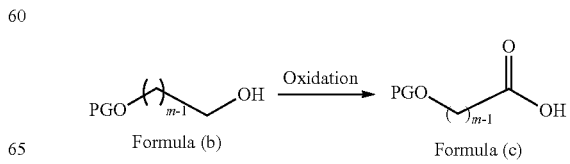

(3) The carboxylic acid as shown in Formula (c) is subject to functional group transformation and nucleophilic substitution to introduce the R³ and R⁴ groups. Either of the following two methods can be selected:

(3a) The carboxylic acid is reacted with an alcohol (R'OH) and converted into an ester. This esterification can use various conditions, including esterification under various acidic or alkaline conditions. Subsequently, a nucleophilic substitution is conducted to introduce the R³ and R⁴ groups.

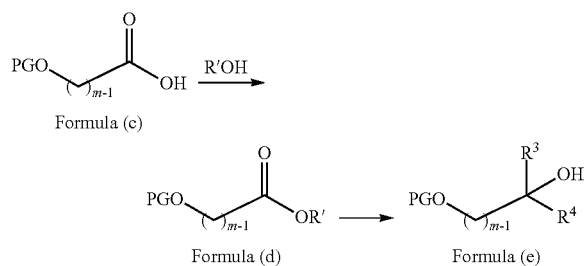

The R' is alkyl, for example, C1-C36 linear or branching alkyl, for example, C1-C18 linear or branching alkyl, for example, C1-C8 linear or branching alkyl.

The most commonly used nucleophilic substituting reagent is the Grignard reagent. The Formula (d) compound can be subject to one-step nucleophilic substitution with the participation of corresponding Grignard reagents, and in the resulting Formula (e) compound, R³=R⁴. Also, by way of stepwise addition of different Grignard reagents, different R³ and R⁴ groups can be introduced.

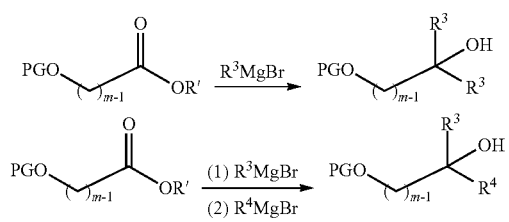

(3b) The carboxylic acid is converted to an acyl halide including groups such as acyl chloride, acyl bromide etc., then the nucleophilic substitution can be conducted to introduce the R³ and R⁴ groups.

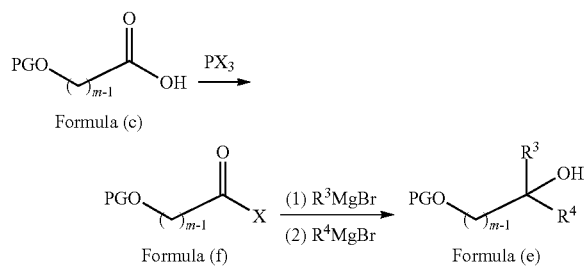

The X is halogen, for example, Cl and Br.

In Schemes (3a) and (3b), the nucleophilic substituting reagent, in addition to the Grignard reagent, can be selected from other nucleophilic substituting reagents, such as alkyl lithium reagent (R³Li), alkyl copper lithium reagent (R³CuLi), etc.

(4) R⁵ is introduced using different methods according to different types of the R⁵ group:

(4a) When R⁵ is alkoxy, a strong alkaline can react with an alcohol hydroxyl to generate an oxygen anion, which is subsequently subject to a nucleophilic substitution by R⁵'X.

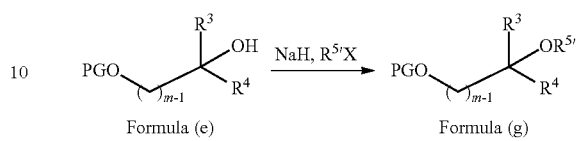

The X is a halogen atom (F, Cl, Br, I), trifluoromethanesulfonate group or p-toluenesulfonate group.

The R⁵' is selected from alkyl.

(4b) When R⁵ is alkyl, halogen substituted alkoxy, alkenyl or alkynyl, the Formula (c) compound can be first reacted with trifluoromethanesulfonyl chloride to generate a good leaving group trifluoromethanesulfonate group, and then the substitution is conducted by nucleophilic substitution.

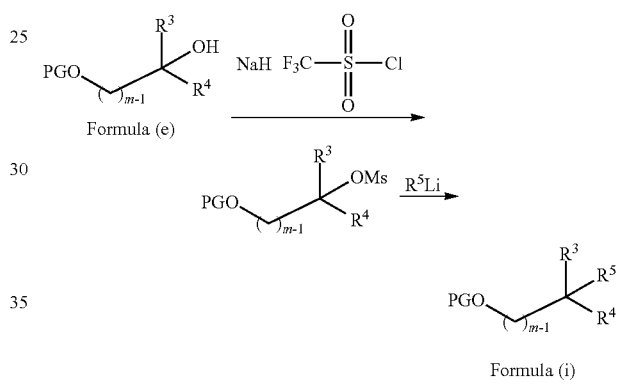

(4c) When R⁵ is a hydrogen atom, the oxygen atom can be removed under the conditions of triethylsilane (Et₃SiH) and trifluoroacetic acid.

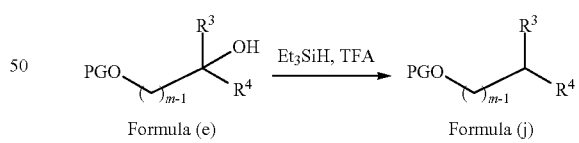

(5) The protecting group is eliminated to generate the corresponding alcohol:

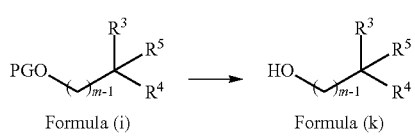

When the protecting group is a benzyl protecting group, silicon protecting group, methoxymethyl protecting group (MOM), tetrahydropyran protecting group (THP), p-methoxyphenyl (PMB) protecting group, etc, the corresponding method for removing it in the prior art can be selected to remove the protecting group to generate the corresponding alcohol, for example:

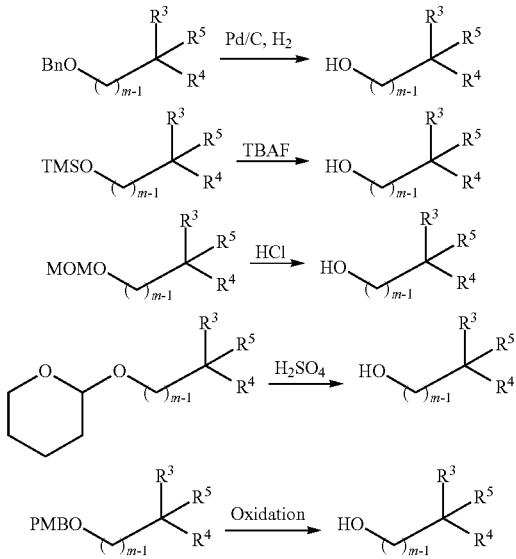

(6) The hydroxyl at position R can be subject to many types of substitution to convert to corresponding functional group, such as halogen, amino, cyano, azide group, trifluoromethanesulfonate group (MsO), p-toluenesulfonate group (TsO), alkenyl, alkynyl, and alkoxy, etc.

(6a) When R is halogen, the following reactions can be conducted, but they are not limited to these reactions.

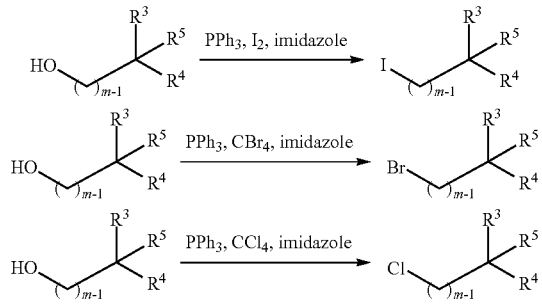

(6b) When R is trifluoromethanesulfonate group (MsO) or p-toluenesulfonate group (TsO), an alkaline can react with an alcohol hydroxyl to generate an oxygen anion, which is subsequently subject to a nucleophilic substitution by MsCl or TsCl.

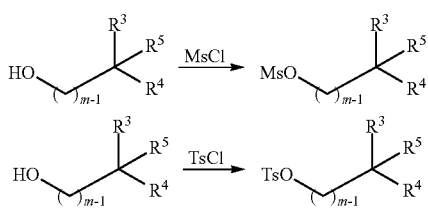

(6c) When R is an azide group ($N_3$), it can be obtained by a nucleophilic substitution between sodium azide ($NaN_3$) and halogen, trifluoromethanesulfonate group (MsO) or p-toluenesulfonate group (TsO):

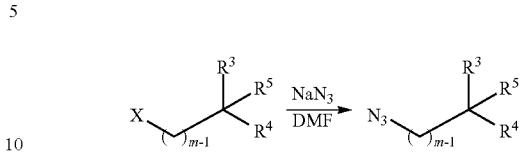

In the aforementioned equation, X represents a halogen atom, trifluoromethanesulfonate group or p-toluenesulfonate group.

(6d) When R is cyano, it can be obtained by a nucleophilic substitution between a cyanide (such as sodium cyanide, potassium cyanide) and halogen, trifluoromethanesulfonate group (MsO) or p-toluenesulfonate group (TsO):

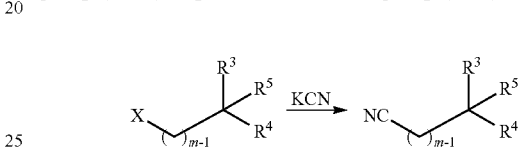

In the aforementioned equation, X represents a halogen atom, trifluoromethanesulfonate group or p-toluenesulfonate group.

(6e) When R is amino group, the azide group or cyano group can be reduced to amino group, or it can be obtained by Gabriel amine synthesis.

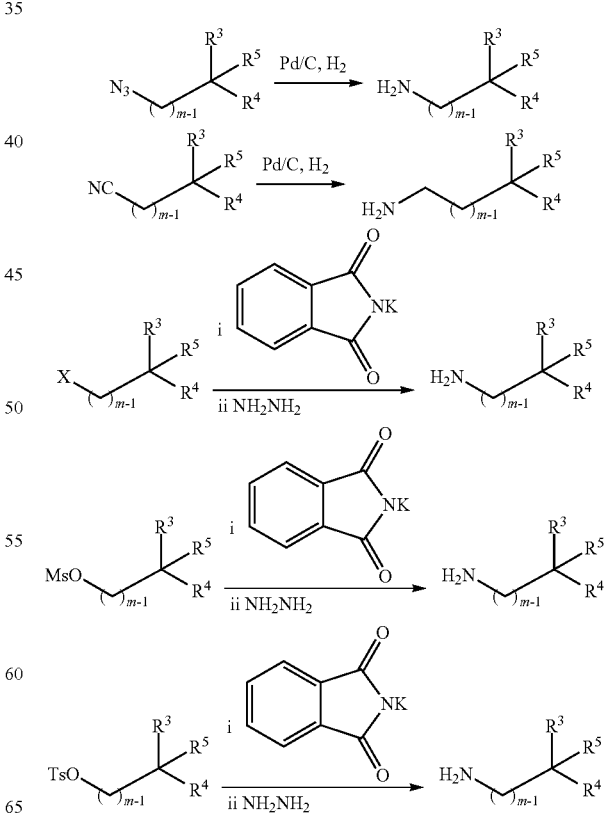

(6f) When R is an alkenyl or alkynyl, it can be obtained by a nucleophilic substitution with a nucleophilic agent containing the alkenyl or alkynyl such as RLi, for example:

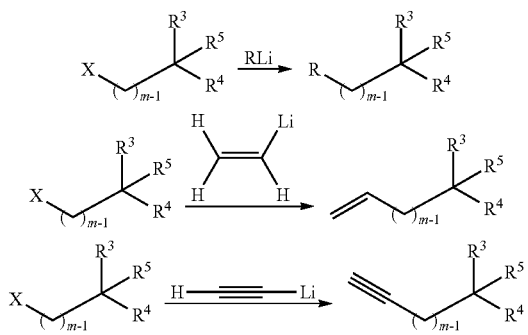

The branching alkyl chain in the aforementioned compounds as shown in Formula (I) can serve as a solubilizing group for the preparation of the organic conjugated molecules (especially the organic conjugated polymers) and increase the mobility of carriers in the organic conjugated molecule materials. Further, these organic conjugated molecules, serving as organic semiconductor materials, can be applied to photoelectric devices such as organic solar cells, organic light emitting diodes, and organic field effect transistors, etc.

In the second aspect of the invention, polymers with the aforementioned branching alkyl chains as shown in the following Formula (II) are provided:

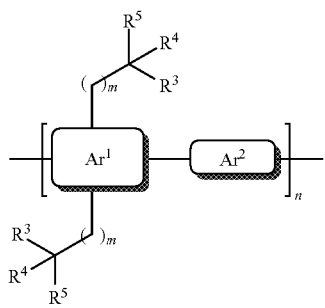

Formula (II)

In Formula (II), $Ar^1$ and $Ar^2$ represent different aromatic compound fragments; n is an integer which represents the polymerization degree of the polymer.

Wherein $Ar^1$ contains one or more branching alkyl chains in the compounds as shown in the General Formula (I).

n can, for example, be an integer of 1~1,000,000, an integer of 1~10,000, or an integer of 1~1,000.

The polymer is obtained by polymerization of the $Ar^1$ and $Ar^2$ monomers. The polymerization can be conducted by coupling, for example, Suzuki coupling, Stille coupling, Negishi coupling, Sonogashira coupling, Heck coupling, Kumada coupling, Hiyama coupling, Buchwald-Hartwig coupling and carbon-hydrogen bond activation coupling (Berrouard, P.; Najari, A.; Pron, A.; Gendron, D.; Morin, P.-O.; Pouliot, J.-R.; Veilleux, J.; Leclerc, M. *Angew. Chem., Int. Ed.* 2011, 51, 2068), etc., for example. Suzuki coupling, Stifle coupling, Sonogashira coupling, Heck coupling, Kumada coupling and carbon-hydrogen bond activation coupling.

In an embodiment of the invention, the number of methylenes between the alkyl side chain and the backbone in the polymer, i.e., m>1, for example, m can be an integer of 2~18, an integer of 2~10, an integer of 3~18, an integer of 3~10, an integer of 3~5, or an integer of 3~4. This can effectively reduce the effect of the alkyl chains on the π-π stacking of the polymer backbone, thereby greatly increasing the mobility of the polymer.

The polymer as shown in Formula (II) is polymerized from the aromatic compound monomer having the branching alkyl chains as shown in the following Formula (III) and the $Ar^2$ aromatic compound monomers. The wavy line in Formula (III) indicates the functional group required by the monomers to polymerize, for example, in order to perform Suzuki coupling, the functional group can be a halogen, boric acid or borate; in order to perform Stille coupling, the functional group can be a halogen or alkyl tin; in order to perform Sonogashira coupling, the functional group can be a halogen or ethynyl; in order to perform Fleck coupling, the functional group can be a halogen or ethenyl; in order to perform Kumada coupling, the functional group is a halogen; in order to perform carbon-hydrogen bond activation coupling, the functional group can be a halogen or hydrogen; and in order to perform Hiyama coupling, the functional group can be a halogen or silane.

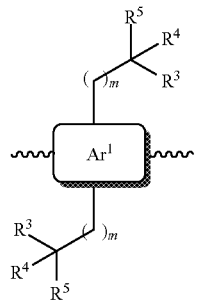

Formula (III)

The aromatic compound as shown in Formula (III) is, for example, the compounds as shown in the following Formulae III-1 to III-16:

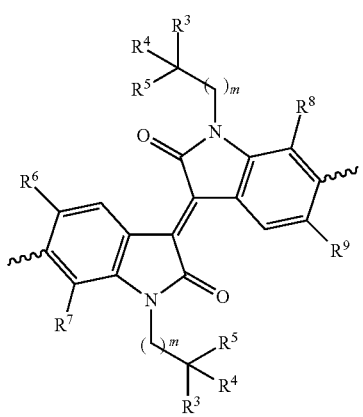

III-1

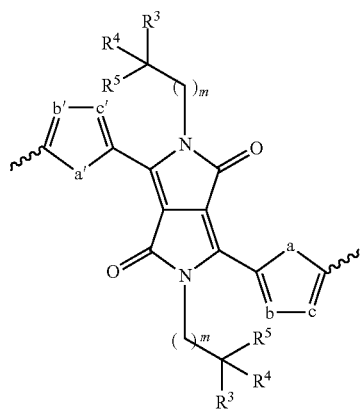
III-2
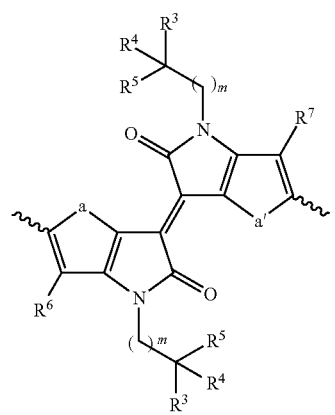
III-3
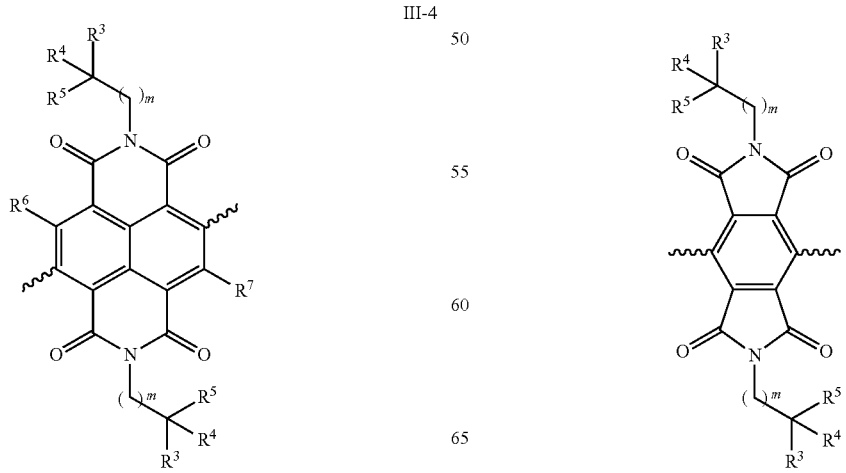
III-4
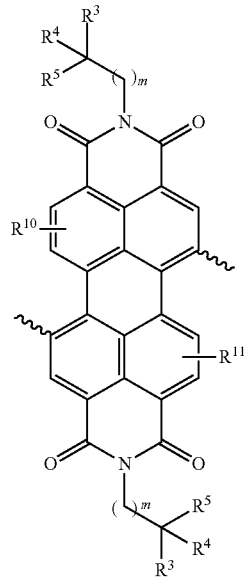
III-5
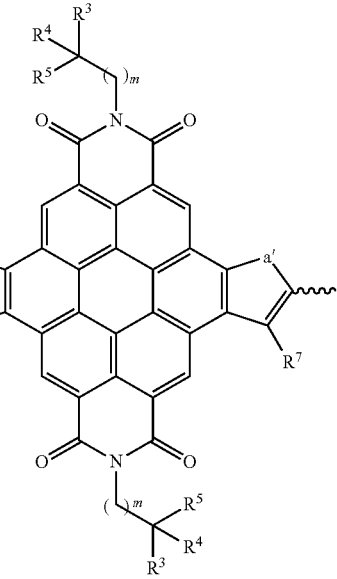
III-6
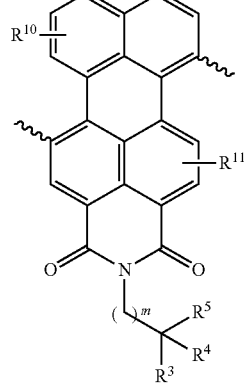
III-7

-continued

III-8

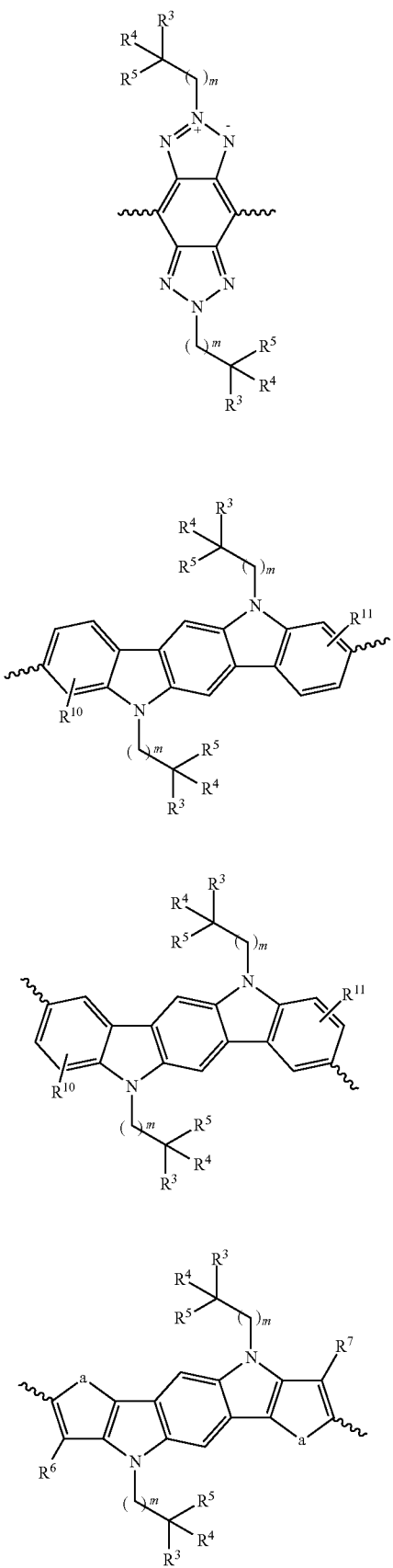

III-9

III-10

III-11

-continued

III-12

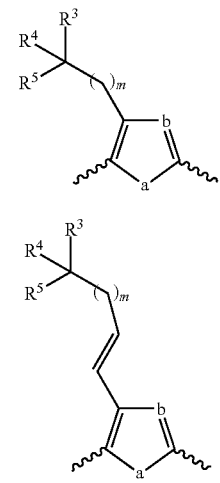

III-13

III-14

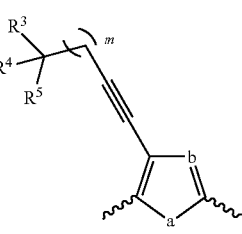

III-15

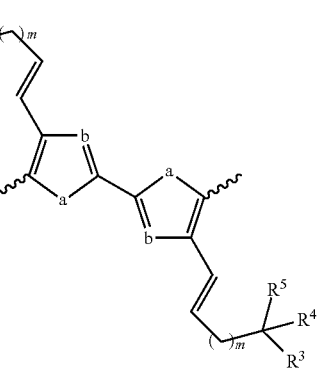

III-16

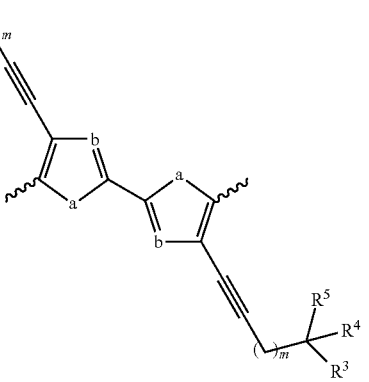

$R^6$, $R^7$, $R^8$, and $R^9$ represent substituents on the aromatic ring, for example, hydrogen atom, halogen atom (such as F, Cl, etc.), nitro, amino, cyano, alkyl, alkenyl, alkynyl, alkoxy, halogen substituted alkyl, halogen substituted alkoxy, etc.

$R^{10}$ and $R^{11}$ represent one or more substituents on the aromatic ring, for example, hydrogen atom, halogen atom (such as F, Cl, etc.), nitro, amino, cyano, alkyl, alkenyl, alkynyl, alkoxy, halogen substituted alkyl, halogen substituted alkoxy, etc.

a and a' can be independently selected from the following structures: —S—, —O—, —Se—, —NR$^{12}$—, etc.

b, b', c and c' can be independently selected from the following structures: —N=, =N—, —CR$^{12}$=, =CR$^{12}$—, etc.

The aforementioned R$^{12}$ represents hydrogen atom, alkyl, alkenyl, alkynyl, alkoxy, halogen substituted alkyl, halogen substituted alkoxy, aryl or heteroaryl, etc.

The aforementioned alkyl can, for example, be C1-C36 linear or branching alkyl, for example, C1-C18 linear or branching alkyl.

The aforementioned halogen substituted alkyl, can for example, be C1-C36 linear or branching halogen substituted alkyl, for example, C1-C18 linear or branching halogen substituted alkyl.

The aforementioned alkoxy can, for example, be C1-C36 linear or branching alkoxy, for example. C1-C18 linear or branching alkoxy.

The aforementioned halogen substituted alkoxy can, for example, be C1-C36 linear or branching halogen substituted alkoxy, for example, C1-C18 linear or branching halogen substituted alkoxy.

The aforementioned alkenyl can, for example, be C2-C18 alkenyl, C2-C10 alkenyl, or C2-C6 alkenyl.

The aforementioned alkynyl can, for example, be C2-C18 alkynyl, C2-C10 alkynyl, or C2-C6 alkynyl.

The aforementioned aryl can, for example, be phenyl or substituted phenyl, for example, phenyl.

The aforementioned heteroaryl can, for example, be thienyl, thiazolyl, pyridyl, furyl, for example, thienyl or thiazolyl.

The Ar$^2$ aromatic compound monomer can be selected from the follow structures:

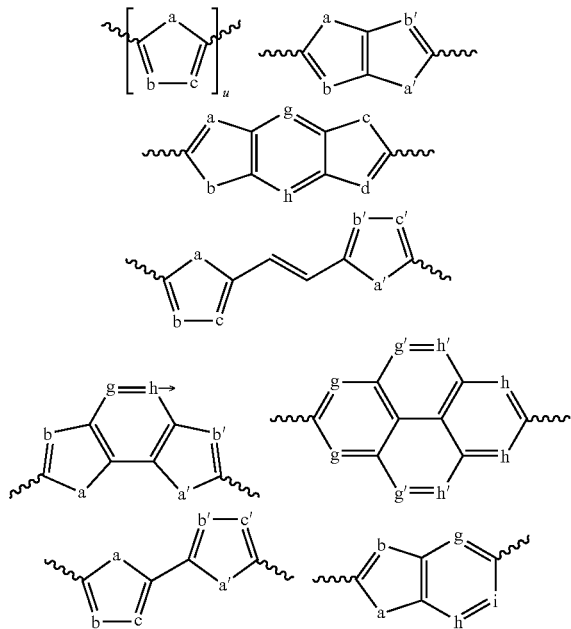

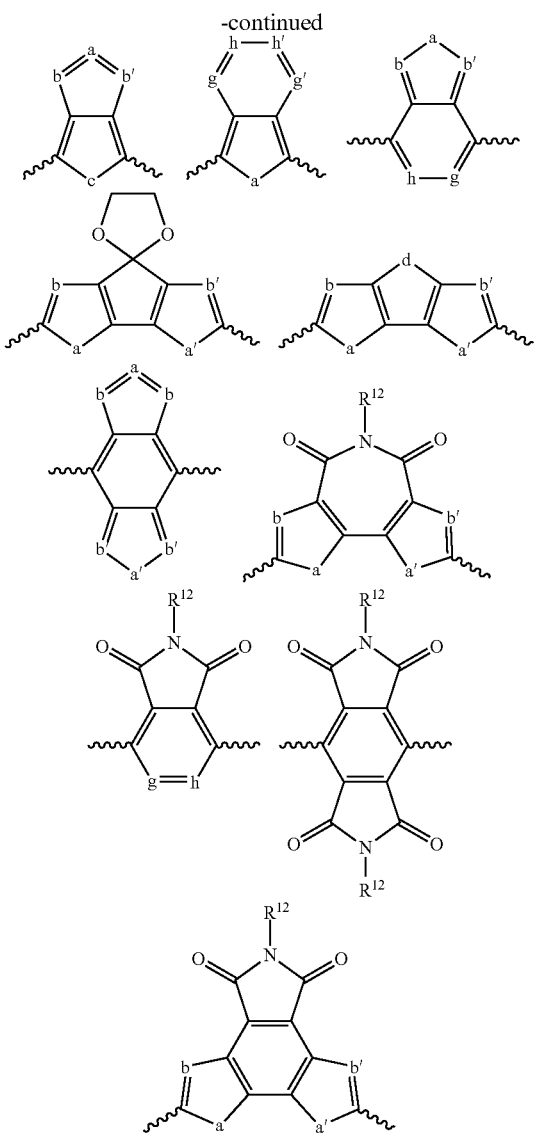

wherein the wavy line indicates the functional group required for the polymerization with the Ar$^1$ monomers;

a and a' can be independently selected from the following structures: —S—, —Se—, —O— and —NR$^{12}$—;

b and b' can be independently selected from the following structures: —N=, =N—, —SiR$^{12}$=, =SiR$^{12}$—, —SiR$^{12}$R$^{12}$—, —CR$^{12}$R$^{12}$—CR$^{12}$R$^{12}$— and —CR$^{12}$=CR$^{12}$—;

c can be selected from the following structures: —S—, —S(O)—, —S(O)$_2$—, —O—, —N=, =N—, —SiR$^{12}$=, =SiR$^{12}$—, —SiR$^{12}$R$^{12}$—, —CR$^{12}$R$^{12}$—CR$^{12}$R$^{12}$—, —CR$^{12}$=CR$^{12}$—;

d can be selected from the following structures: —S—, —S(O)—, —S(O)$_2$—, —O—, —N=, =N—, —SiR$^{12}$=, =SiR$^{12}$—, —SiR$^{12}$R$^{12}$—, —CR$^{12}$R$^{12}$—CR$^{12}$R$^{12}$—, —CR$^{12}$=CR$^{12}$—, —C(O)— and —C(C(CN)$_2$)—;

g, h, g' and h' can be independently selected from the following structures: —CR$^{12}$=, =CR$^{12}$—, —C—, —C(O)— and —C(C(CN)$_2$)—, —N= and =N—;

The aforementioned R$^{12}$ can be hydrogen atom, alkyl, alkenyl, alkynyl, alkoxy, halogen substituted alkyl, halogen substituted alkoxy, aryl or heteroaryl etc.;

u is 1, 2, 3 or 4.

The Ar² aromatic compound monomer can, for example, be one of the following structures:
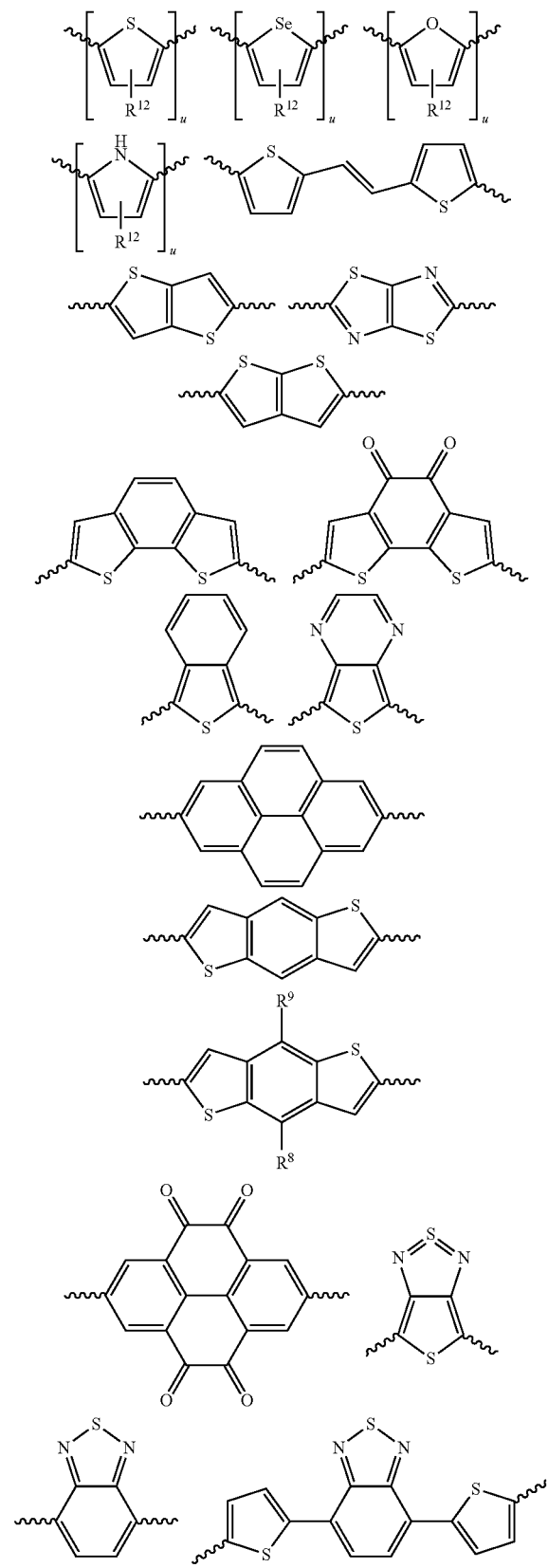
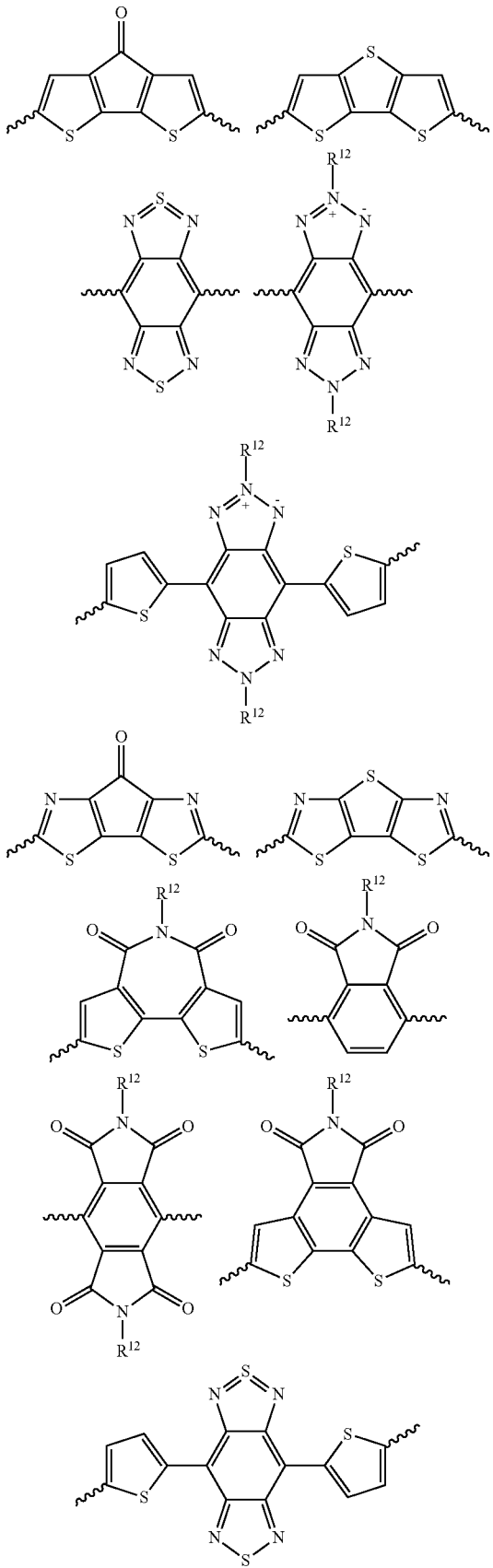

$R^{12}$ can be hydrogen atom, alkyl, alkenyl, alkynyl, alkoxy, halogen substituted alkyl, halogen substituted alkoxy, aryl or heteroaryl, etc.; u is 1, 2, 3 or 4.

The aforementioned $Ar^2$ aromatic compound can have one or more substituents in its structure.

The synthesis of the $Ar^1$ aromatic compound having the branching alkyl chains can be started from aromatic compounds known in the literature, and obtained by reacting these compounds with the halide and amino compounds, etc. having the branching alkyl chain structure in the present disclosure. Specifically, there are the five following schemes:

(1) When the R in Formula (I) is halogen (X), a nucleophilic substitution can occur between X and the following nitrogen-containing aromatic compounds to prepare the aromatic compound in the General Formula (III), for example:

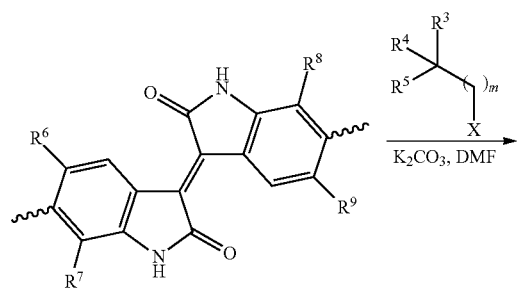

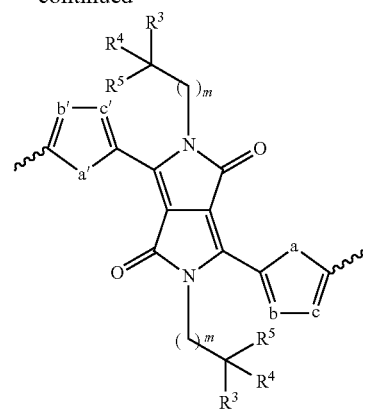

III-2

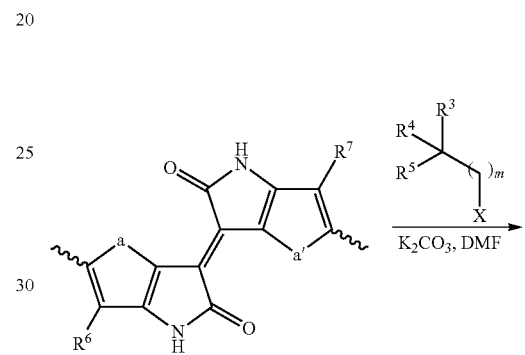

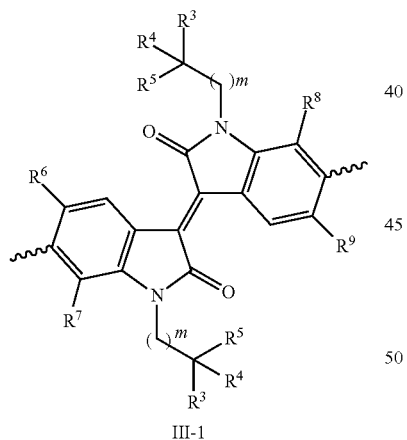

III-1

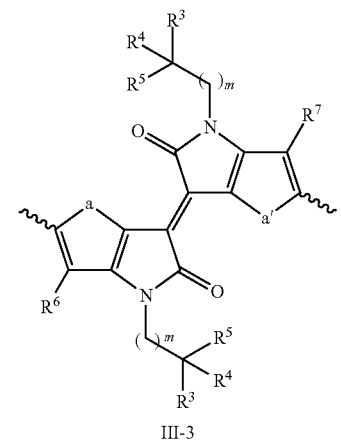

III-3

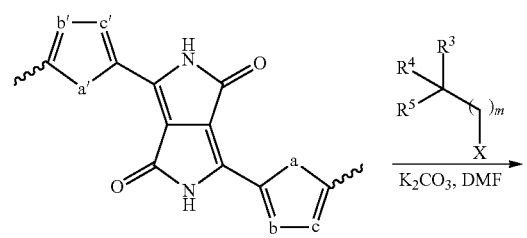

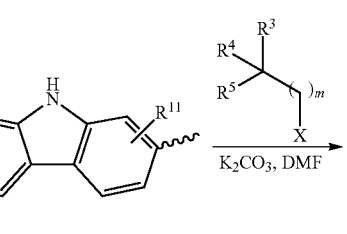

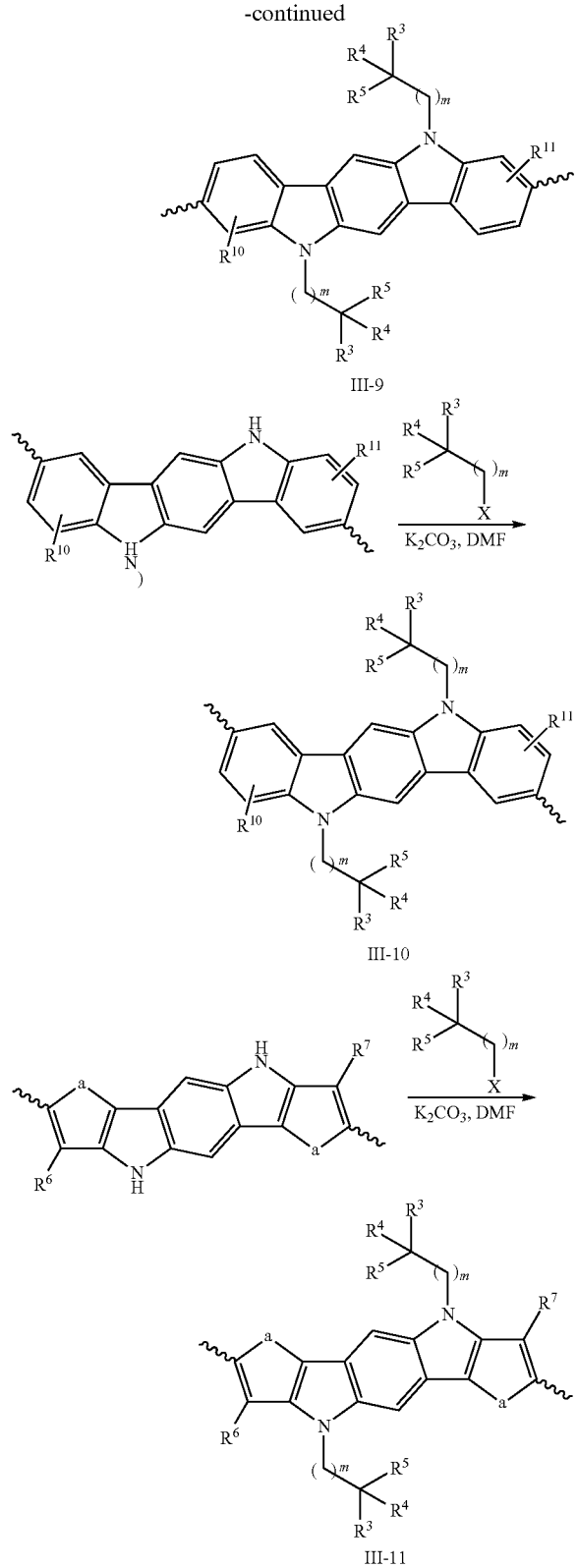

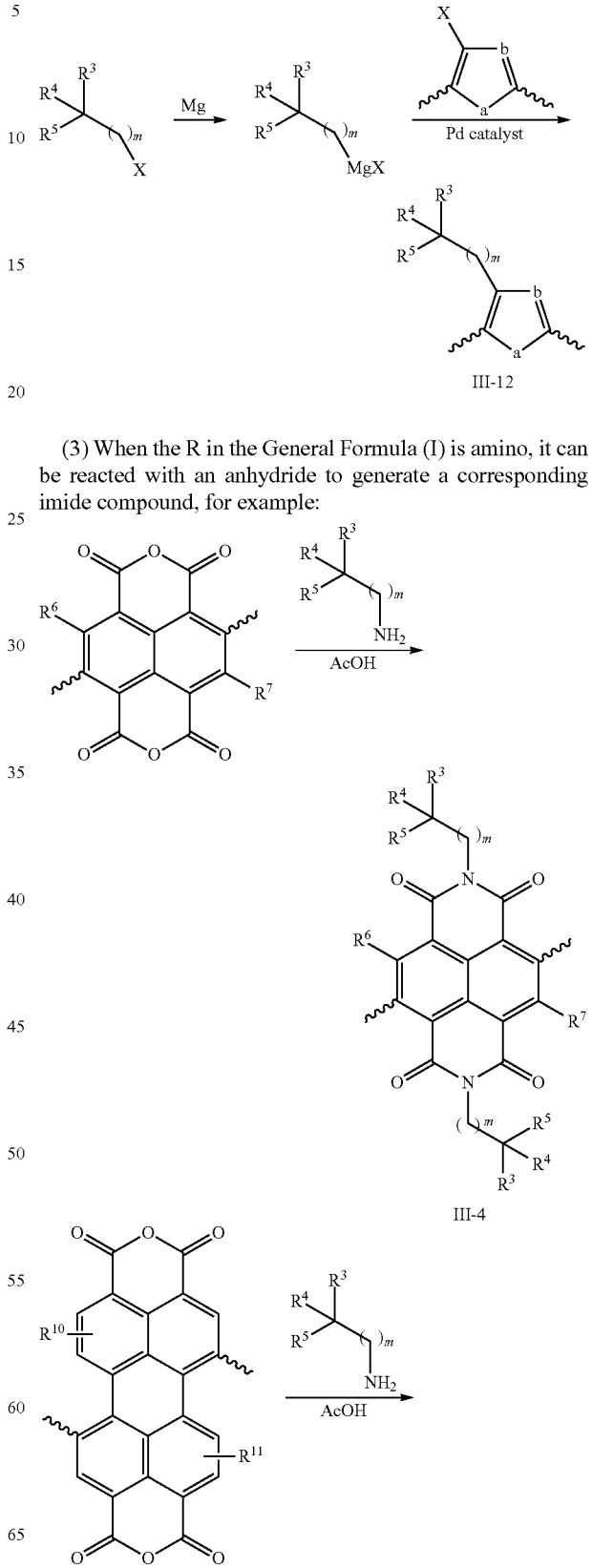

(2) When the R in the General Formula (I) is trifluoromethanesulfonate group (MsO) or p-toluenesulfonate group (TsO), because these good leaving groups have similar properties to halogen, they can also be used in the nucleophilic substitution reaction as shown in (1).

(3) When the R in the General Formula (I) is halogen (X), X is Br or I for preparing the corresponding Grignard reagent, thereby directly obtaining the alkyl substituted aromatic compound via Kumada coupling, for example:

(3) When the R in the General Formula (I) is amino, it can be reacted with an anhydride to generate a corresponding imide compound, for example:

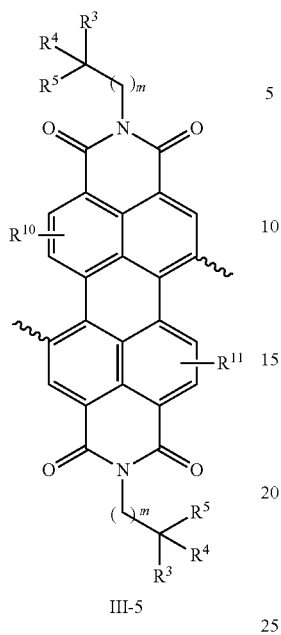
III-5
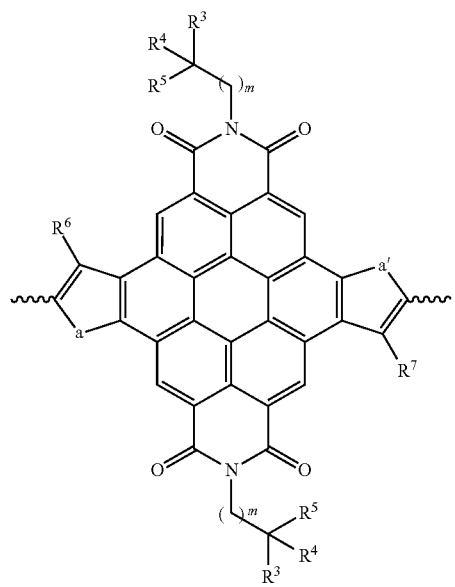
III-6
The III-6 type compounds can be prepared from III-5 via multi-step reactions based on the prior art.
(4) When the R in the General Formula (I) is alkenyl, a Heck reaction can occur between it and an aromatic halide (X═Cl, Br or I) to obtain the corresponding arylalkenyl derivatives, for example:
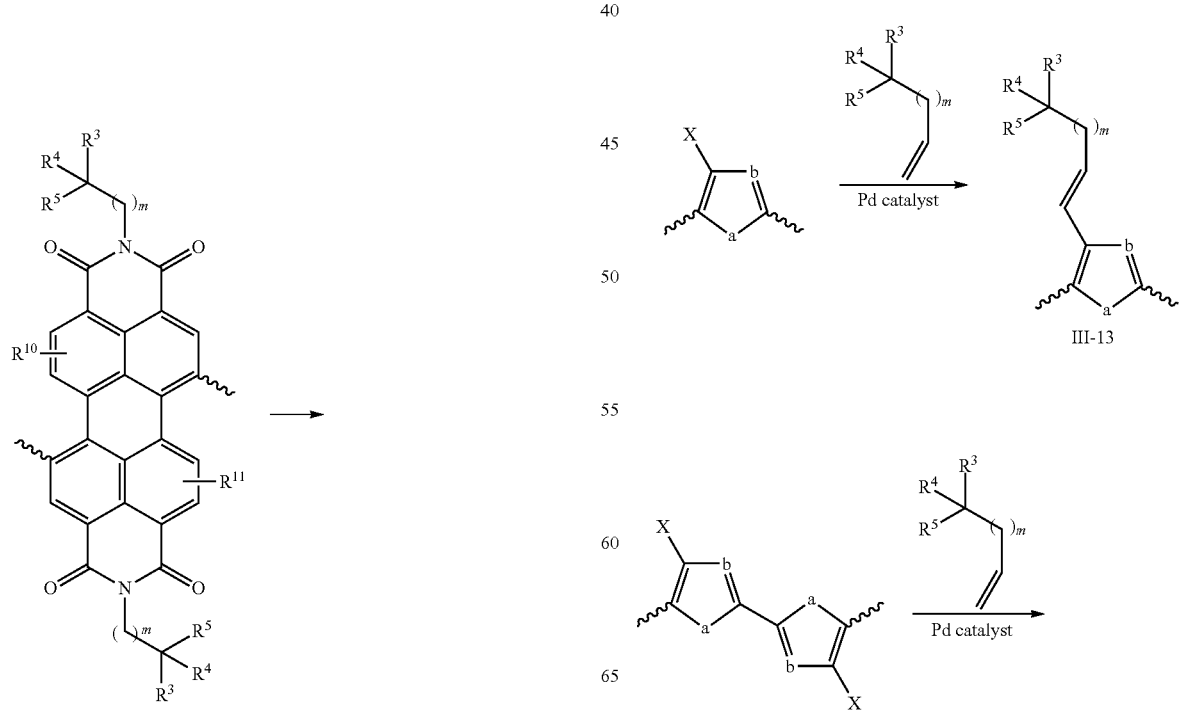
III-13

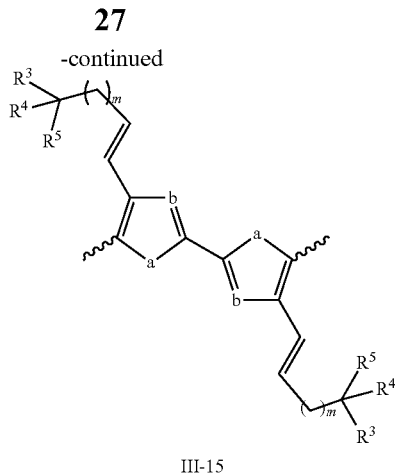

III-15

(5) When the R in the General Formula (I) is alkynyl, Sonogashira reaction can occur between it and an aromatic halide (X=Cl, Br or I) to obtain the corresponding arylalkynyl derivatives, for example:

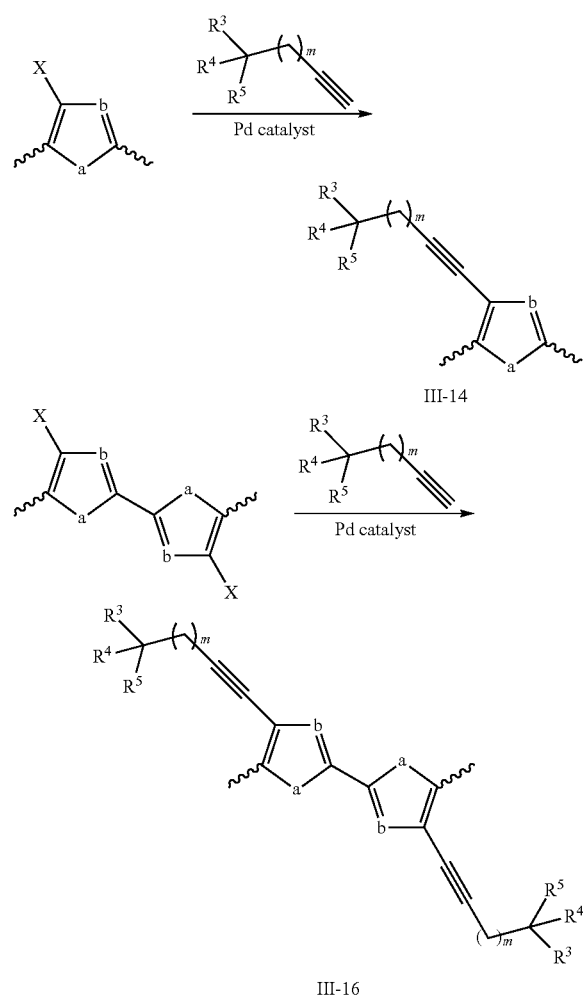

III-16

In the third aspect of the invention, the aforementioned polymer having the branching alkyl chain as shown in Formula (II), serving as an organic semiconductor material, can be applied to photoelectric devices such as organic field effect transistors, organic solar cells, and organic light emitting diodes, etc., proving that it can greatly increase the mobility of carriers in the organic semiconductor materials.

In the invention, compounds containing a type of novel branching alkyl chains have been designed, and effective synthetic schemes of the compounds containing this type of novel branching alkyl chains have been raised which enables easy transformation of functional groups. In the invention, it is further proved that compounds having this type of branching alkyl chains can be applied to organic conjugated polymers, and can effectively adjust the π-π stacking between molecules, also change the spectral properties and electrochemical properties of the polymers, and significantly increase the mobility of the organic electronic materials. Therefore, these results can be widely used in the field of organic electronics, including the field of organic photovoltaic cells (OPV), organic light emitting diodes (OLED), and organic field effect transistors, etc.

DETAILED DESCRIPTION

Figure 1:
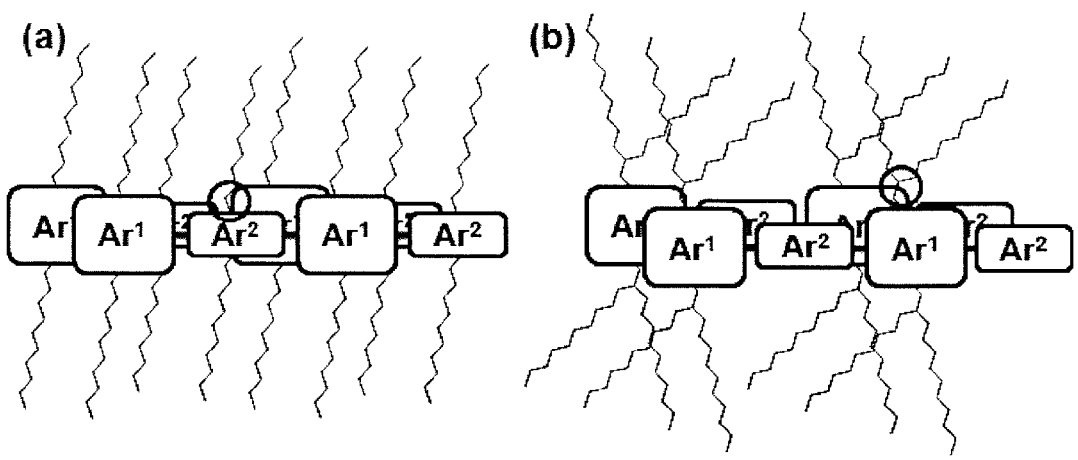
FIG. 1 shows the effect of the position of the solubilizing group (such as the alkyl chain) on the π-π stacking of the organic conjugated polymers.
Figure 2:
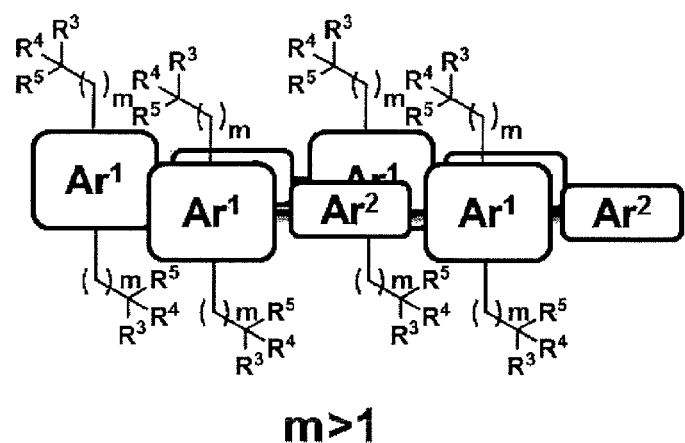
FIG. 2 shows the structural diagram of the organic conjugated polymer having the branching alkyl chains according to an embodiment of the invention.

The invention is further described in details by way of examples in relation to figures. However, they are by no means limiting the scope of the invention.

Example 1 to Example 3 are Method for Synthesizing Alcohols Protected by Benzyloxy Example 1

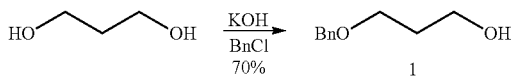

Scheme for Synthesizing Compound 1: 1,3-propanediol (60 g, 0.79 mol) was added into a 500 ml round bottom flask, then solid KOH (17.7 g, 0.32 mol) was added to remove the trace moisture in the 1,3-propanediol. Under agitation at 90° C., benzyl chloride (39.8 g, 0.32 mol) was added into the 1,3-propanediol using a dropping funnel. Then temperature was increased to 130° C. for a 2h reaction. The reaction was stopped and cooled to the room temperature. After extraction of the organic phase using water/diethyl ether separation, the solvent was removed by reduced pressure rotatory evaporation, followed by reduced pressure distillation. 39.8 g colorless oily product Compound 1 was obtained with a yield of 77%. $^1$H NMR (CDCl$_3$, 400 MHz, ppm) δ: 7.36-7.28 (m, 5H), 4.51 (s, 2H), 3.79-3.75 (m, 2H), 3.66-3.64 (t, J=5.5 Hz, 2H), 2.44 (br. s, 1H), 1.88-1.83 (m, 2H).

Example 2

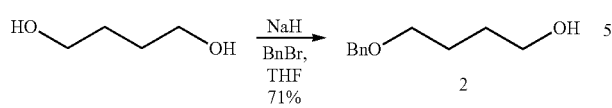

Scheme for Synthesizing Compound 2: At 0° C., 1,4-butanediol (40 g, 0.44 mol) was added into 200 ml dry THF. Sodium hydride (5.3 g, 0.22 mol) was added in batches within 30 min. The temperature returned to the room temperature for a 2h reaction. Benzyl bromide (38 g, 0.22 mol) was dissolved in 20 ml THF, which was dropped into the aforementioned system at 0° C. followed by reflux for 4 h. After the complete of the reaction, the reaction was quenched with cold water. The organic phase was extracted with diethyl ether. After drying the organic phase with anhydrous sodium sulfate, it was filtered, then subject to reduced pressure rotatory evaporation to remove the solvent, followed by reduced pressure distillation to obtain 28.1 g of colorless oily liquid 2 with a yield of 71%.

$^1$H NMR (CDCl$_3$, 400 MHz, ppm) δ: 7.36-7.26 (m, 5H), 4.52 (s, 2H), 3.65-3.61 (m, 2H), 3.53-3.50 (t, J=5.3 Hz, 2H), 2.36 (br. s, 1H), 1.73-1.65 (m, 4H).

Example 3

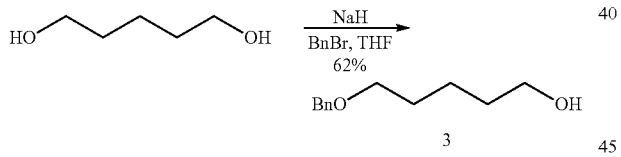

Scheme for Synthesizing Compound 3: At 0° C., 1,5-pentanediol (40 g, 0.39 mol) was added into 200 ml dry THF. Sodium hydride (4.6 g, 0.19 mol) was added in batches within 30 min. The temperature returned to the room temperature for a 2 h reaction. Benzyl bromide (33 g, 0.19 mol) was dissolved in 20 ml THF, which was dropped into the aforementioned system at 0° C. followed by reflux for 4 h. After the complete of the reaction, the reaction was quenched with cold water. The organic phase was extracted with diethyl ether. After drying the organic phase with anhydrous sodium sulfate, it was filtered, then subject to rotatory evaporation to remove the solvent, followed by reduced pressure distillation to obtain 23.1 g of colorless oily liquid 3 with a yield of 62%. $^1$H NMR (CDCl$_3$, 400 MHz, ppm) δ: 7.36-7.26 (m, 5H), 4.50 (s, 2H), 3.64-3.61 (t, J=6.5 Hz, 2H), 3.50-3.64 (t, J=6.5 Hz, 2H), 1.68-1.54 (m, 4H), 1.49-1.43 (m, 2H).

Example 4 to Example 6 are the Jones Oxidation and Protection by Esterification of the Alcohols Protected by Benzyloxy

Example 4

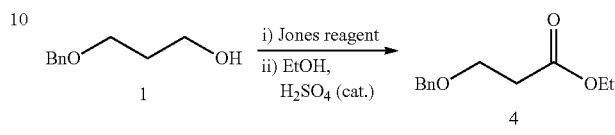

Scheme for Synthesizing Compound 4: Compound 1 (10 g, 60.2 mmol) was dissolved into 200 ml acetone. At 0° C. Jones reagent (26.72 g chromium trioxide: 23 ml concentrated sulfuric acid, diluted with water to 100 ml) was added dropwise until the orange red color was sustained without turning green. The temperature returned to the room temperature followed by agitation for 2h. The resultant mixture was vacuum suck filtrated and loaded onto a column which was eluted with acetone. After acetone was removed by vacuum rotatory evaporation, the organic phases were extracted with ethyl acetate for three times. The organic phases were combined and washed once with saturated saline. After dried with anhydrous sodium sulfate and rotatory evaporation, 100 ml ethanol and 2 ml concentrated H$_2$SO$_4$ were added for 12 h reflux reaction. After most solvent was removed by rotatory evaporation, water/ethyl acetate phase separation was conducted. The organic phase was washed with sodium bicarbonate solution, water, and saturated saline respectively, and then dried with anhydrous sodium sulfate. After the solvent was removed by rotatory evaporation, reduced pressure distillation was conducted to obtain 9.7 g colorless oily liquid 4 with a yield of 77%. $^1$H NMR (CDCl$_3$, 400 MHz, ppm) δ: 7.36-7.28 (m, 5H), 4.54 (s, 2H), 4.17-4.13 (q, J=7.0 Hz, 2H), 3.77-3.74 (t, J=6.2 Hz, 2H), 2.63-2.60 (t, J=6.2 Hz, 2H), 1.28-1.24 (t, J=7.1 Hz, 3H).

Example 5

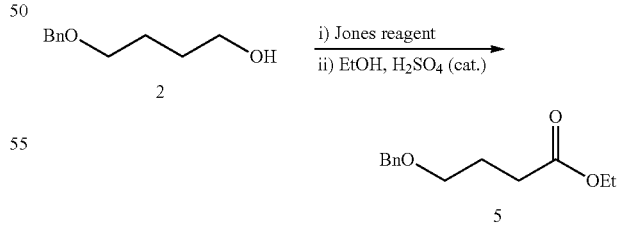

Scheme for Synthesizing Compound 5: Compound 2 (26.6 g) was dissolved into 200 ml acetone. At 0° C., Jones reagent was added dropwise until the orange red color was sustained without turning green. The temperature returned to the room temperature followed by agitation for 2h. The resultant mixture was vacuum suck filtrated and loaded onto a column which was eluted with acetone. After acetone was removed by vacuum rotatory evaporation, the organic phases were extracted with ethyl acetate for three times. The organic phases were combined and washed once with saturated saline. After dried with anhydrous sodium sulfate and rotatory evaporation, 100 ml ethanol and 2 ml concentrated H₂SO₄ were added for 12 h reflux reaction. After most solvent was removed by rotatory evaporation, water/ethyl acetate phase separation was conducted. The organic phase was washed with sodium bicarbonate solution, water, and saturated saline respectively, and then dried with anhydrous sodium sulfate. After the solvent was removed by rotatory evaporation, reduced pressure distillation was conducted to obtain 24.2 g colorless oily liquid 5 with a yield of 70%. $^1$H NMR (CDCl₃, 400 MHz, ppm) δ: 7.36-7.27 (m, 5H), 4.49 (s, 2H), 4.14-4.08 (q, J=7.1 Hz, 2H), 3.52-3.49 (t, J=6.1 Hz, 2H), 2.44-2.40 (t, J=7.3 Hz, 2H), 1.97-1.91 (m, 2H), 1.26-1.22 (t, J=7.1 Hz, 3H).

Example 6

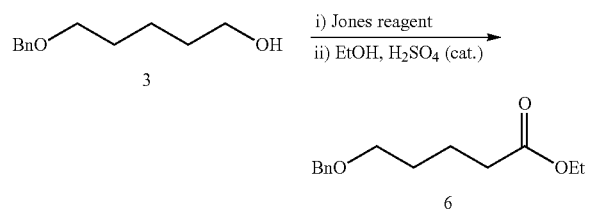

Scheme for Synthesizing Compound 6: Compound 3 (23.1 g) was dissolved into 200 ml acetone. At 0° C., Jones reagent was added dropwise until the orange red color was sustained without turning green. The temperature returned to the room temperature followed by agitation for 2h. The resultant mixture was vacuum suck filtrated and loaded onto a column which was eluted with acetone. After acetone was removed by vacuum rotatory evaporation, the organic phases were extracted with ethyl acetate for three times. The organic phases were combined and washed once with saturated saline. After dried with anhydrous sodium sulfate and rotatory evaporation, 100 ml ethanol and 2 ml concentrated H₂SO₄ were added for 12 h reflux reaction. After most solvent was removed by rotatory evaporation, water/ethyl acetate phase separation was conducted. The organic phase was washed with sodium bicarbonate solution, water, and saturated saline respectively, and then dried with anhydrous sodium sulfate. After the solvent was removed by rotatory evaporation, reduced pressure distillation was conducted to obtain a colorless oily liquid 6 with a yield of 62%. $^1$H NMR (CDCl₃, 400 MHz, ppm): δ 7.36-7.28 (m, 5H), 4.50 (s, 2H), 4.15-4.09 (q, J=6.8 Hz, 2H), 3.50-3.47 (t, J=5.8 Hz, 2H), 2.34-2.30 (t, J=7.0 Hz, 2H), 1.73-1.65 (m, 4H), 1.27-1.23 (t, J=6.9 Hz, 3H). $^{13}$C NMR (CDCl₃, 100 MHz, ppm): δ 173.50, 138.48, 128.28, 127.52, 127.44, 72.82, 69.78, 60.14, 34.00, 29.11, 21.72, 14.19. ESI-HRMS: Calcd. for [M+H]⁺: 237.14852. Found: 237.14859. Calcd. for [M+Na]⁺: 259.13047. Found: 259.13068.

Example 7 to Example 9 are Reactions Between Esters and Grignard Reagents

Example 7

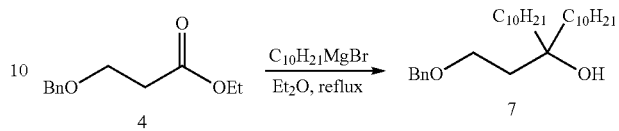

Scheme for Synthesizing Compound 7: Dry magnesium powders (2.88 g, 120 mmol) and an iodine grain were added into a three-necked bottle. Under nitrogen protection, 1-bromodecane (26.5 g, 120 mmol) in diethyl ether solution was added dropwise under room temperature. After the drop addition initiated the reaction, a one hour reflux was conducted. Then under an ice bath, the diethyl ether solution of Compound 4 was added dropwise into the system. After 5 h reflux, it was quenched with H₂SO₄ (2 M) under ice bath, and then extracted with diethyl ether (3×50 mL). After the organic phases were combined, it was washed with water and saturated saline. After dried with anhydrous Na₂SO₄ and rotatory evaporation, it was loaded onto the silica gel column for separation. Compound 7 (12.4 g) was obtained with a yield of 60%. $^1$H NMR (CDCl₃, 400 MHz, ppm): δ 7.35-7.26 (m, 5H), 4.51 (s, 2H), 3.69-3.66 (t, J=6.0 Hz, 2H), 2.98 (s, 1H), 1.79-1.76 (t, J=6.0 Hz, 2H), 1.49-1.37 (m, 4H), 1.33-1.15 (m, 32H), 0.90-0.86 (t, J=6.4 Hz, 6H). $^{13}$C NMR (CDCl₃, 100 MHz, ppm) δ: 137.80, 128.36, 127.67, 74.06, 73.34, 67.25, 39.14, 37.73, 31.89, 30.27, 29.62, 29.60, 29.32, 23.65, 22.65, 14.07. ESI-HRMS: Calcd. for [M-OH]⁺: 429.40909. Found: 429.40925; Calcd. for [M+Na]⁺: 469.40160. Found: 469.40182. Elemental Anal.: Calcd. for C₃₀H₅₄O₂: C, 80.65; H, 12.18. Found: C, 80.61; H, 12.16.

Example 8

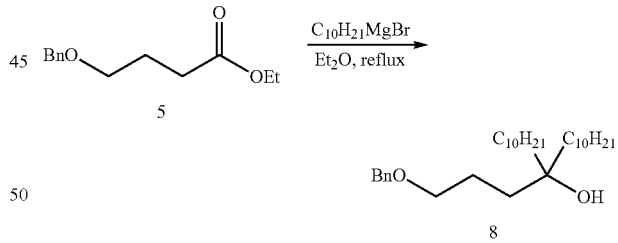

Scheme for Synthesizing Compound 8: Dry magnesium powders and an iodine grain were added into a three-necked bottle. Under nitrogen protection. 1-bromodecane in diethyl ether solution was added dropwise under room temperature. After the drop addition initiated the reaction, a one hour reflux was conducted. Then under an ice bath, the diethyl ether solution of Compound 5 was added dropwise into the system. After 5 h reflux, it was quenched with H₂SO₄ (2 M) under ice bath, and then extracted with diethyl ether (3×50 mL). After the organic phases were combined, it was washed with water and saturated saline. After dried with anhydrous Na₂SO₄ and rotatory evaporation, it was loaded onto the silica gel column for separation. Compound 8 was obtained with a yield of 47%. $^1$H NMR (CDCl₃, 400 MHz, ppm): δ 7.36-7.25 (m, 5H), 4.51 (s, 2H), 3.50-3.47 (t, J=6.3 Hz, 2H), 1.68-1.62 (m, 2H), 1.52-1.48 (m, 2H), 1.43-1.38 (m, 4H), 1.32-1.26 (m, 32H), 0.90-0.86 (t, J=6.4 Hz, 6H) $^{13}$C NMR (CDCl$_3$, 100 MHz, ppm) δ: 138.36, 128.26, 127.51, 127.43, 73.84, 72.83, 70.93, 39.20, 36.05, 31.87, 30.25, 29.61, 29.59, 29.30, 23.87, 23.50, 22.63, 14.05. ESI-HRMS: Calcd. for [M-OH]$^+$: 443.42474. Found: 443.42496; Calcd. for [M+Na]$^+$: 483.41725. Found: 483.41761.

Example 9

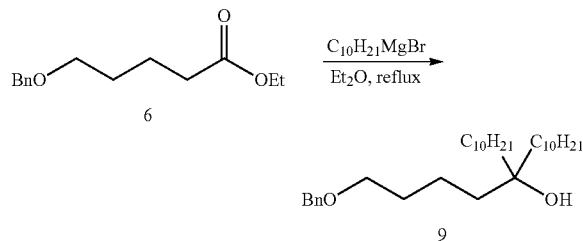

Scheme for Synthesizing Compound 9: Dry magnesium powders and an iodine grain were added into a three-necked bottle. Under nitrogen protection, 1-bromodecane in diethyl ether solution was added dropwise under room temperature. After the drop addition initiated the reaction, a one hour reflux was conducted. Then under an ice bath, the diethyl ether solution of Compound 6 was added dropwise into the system. After 5 h reflux, it was quenched with H$_2$SO$_4$ (2 M) under ice bath, and then extracted with diethyl ether (3×50 mL). After the organic phases were combined, it was washed with water and saturated saline. After dried with anhydrous Na$_2$SO$_4$ and rotatory evaporation, it was loaded onto the silica gel column for separation. Compound 9 was obtained with a yield of 58%. $^1$H NMR (CDCl$_3$, 400 MHz, ppm) δ: 7.35-7.25 (m, 5H), 4.50 (s, 2H), 3.50-3.47 (t, J=6.0 Hz, 2H), 1.63-1.57 (m, 2H), 1.40-1.20 (m, 40H), 1.12 (s, 1H), 0.90-0.86 (t, J=6.4 Hz, 6H). $^{13}$C NMR (CDCl$_3$, 100 MHz, ppm) δ: 138.61, 128.30, 127.60, 127.45, 74.35, 72.88, 70.27, 39.23, 39.04, 31.90, 30.28, 30.26, 29.65, 29.63, 29.61, 29.33, 23.47, 22.67, 20.14, 14.09. ESI-HRMS: Calcd. for [M-OH]$^+$: 457.44094. Found: 457.44063; Calcd. for [M+Na]$^+$: 497.43290. Found: 457.43363.

Example 10 to Example 12 are Deoxygenation and Palladium Carbon Catalyzed Hydrogenation Example 10

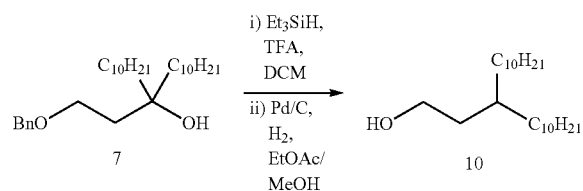

Scheme for Synthesizing Compound 10: Compound 7 (12.4 g, 27.8 mmol) was dissolved into 100 ml dry dichloromethane, to which Et$_3$SiH (3.54 g, 30.5 mmol) and TFA (15.85 g, 139 mmol) were added. After 12 h reaction under the room temperature, Na$_2$CO$_3$ (10 g) was added to quench the reaction until no bubble was generated. It was loaded onto a short silica gel column and eluted with dichloromethane, then a rotatory evaporation was conducted and followed by it was loaded onto a silica gel column for separation to obtain a colorless oily liquid. The resultant colorless oily liquid was dissolved into a mixed solvent of EtOAc/MeOH (100 mL/50 mL), to which 5% Pd/C (0.50 g) catalyst was carefully added. Then the reaction was conducted at the room temperature under one atmospheric pressure of hydrogen gas for 24h. It was loaded onto a flash column and eluted with ethyl acetate, then a rotatory evaporation was conducted and followed by it was loaded onto a silica gel column for separation. A colorless oily liquid 10 was obtained with a yield of 38%. $^1$H NMR (CDCl$_3$, 400 MHz, ppm) δ: 3.68-3.64 (t, J=7.0 Hz, 2H), 1.55-1.50 (q, J=6.8 Hz, 2H), 1.41 (br. s, 1H), 1.32-1.25 (m, 36H), 0.90-0.86 (t, J=6.7 Hz, 6H). $^{13}$C NMR (CDCl$_3$, 100 MHz, ppm) δ: 61.31, 37.01, 34.27, 33.75, 31.92, 30.07, 29.69, 29.65, 29.35. 26.57, 22.69, 14.10. ESI-HRMS: Calcd. for [M+Na]$^+$: 363.35974. Found: 363.35895.

Example 11

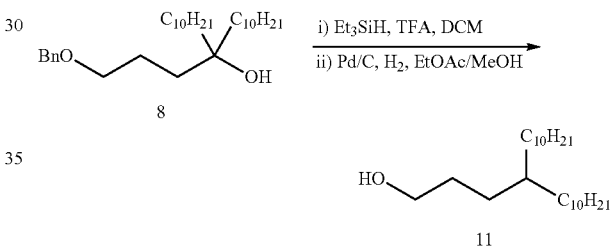

Scheme for Synthesizing Compound 11: Compound 8 was dissolved into 100 ml dry dichloromethane, to which Et$_3$SiH and TFA were added. After 12 h reaction under the room temperature, Na$_2$CO$_3$ was added to quench the reaction until no bubble was generated. It was loaded onto a short silica gel column and eluted with dichloromethane, then a rotatory evaporation was conducted and followed by it was loaded onto a silica gel column for separation to obtain a colorless oily liquid. The resultant colorless oily liquid was dissolved into a mixed solvent of EtOAc/MeOH (100 mL/50 mL), to which 5% Pd/C catalyst was carefully added. Then the reaction was conducted at the room temperature under one atmospheric pressure of hydrogen gas for 24h. It was loaded onto a flash column and eluted with ethyl acetate, then a rotatory evaporation was conducted and followed by it was loaded onto a silica gel column for separation. A colorless oily liquid 11 was obtained with a yield of 67%. $^1$H NMR (CDCl$_3$, 400 MHz, ppm) δ: 3.64-3.61 (t, J=6.6 Hz, 2H), 1.58-1.50 (m, 2H), 1.34-1.24 (m, 39H), 0.90-0.86 (t, J=6.7 Hz, 6H). $^{13}$C NMR (CDCl$_3$, 100 MHz, ppm) δ: 63.48, 37.25, 33.61, 31.92, 30.13, 29.97, 29.71, 29.66, 29.59, 29.35, 26.67, 22.68, 14.07. ESI-HRMS: Calcd. for [M+Na]$^+$: 377.37539. Found: 377.37555.

Example 12

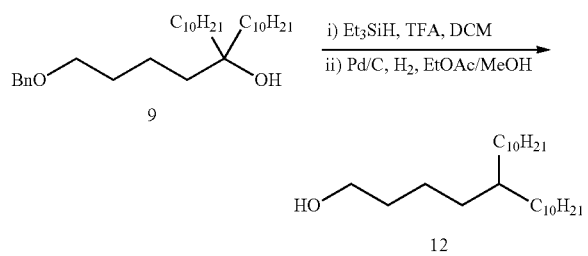

Scheme for Synthesizing Compound 12: Compound 9 was dissolved into 100 ml dry dichloromethane, to which Et$_3$SiH and TFA were added. After 12 h reaction under the room temperature. Na$_2$CO$_3$ was added to quench the reaction until no bubble was generated. It was loaded onto a short silica gel column and eluted with dichloromethane, then a rotatory evaporation was conducted and followed by it was loaded onto a silica gel column for separation to obtain a colorless oily liquid. The resultant colorless oily liquid was dissolved into a mixed solvent of EtOAc/MeOH (100 mL/50 mL), to which 5% Pd/C catalyst was carefully added. Then the reaction was conducted at the room temperature under one atmospheric pressure of hydrogen gas for 24h. It was loaded onto a flash column and eluted with ethyl acetate, then a rotatory evaporation was conducted and followed by it was loaded onto a silica gel column for separation. A colorless oily liquid 12 was obtained with a yield of 60%. $^1$H NMR (CDCl$_3$, 400 MHz, ppm) δ: 3.66-3.63 (t, J=6.6 Hz, 2H), 1.58-1.51 (m, 2H), 1.34-1.23 (m, 41H), 0.90-0.86 (t, J=6.7 Hz, 6H). $^{13}$C NMR (CDCl$_3$, 100 MHz, ppm) δ: 63.10, 37.42, 33.63, 33.53, 33.30, 31.93, 30.14, 29.72, 29.66, 29.36, 26.71, 22.90, 22.69, 14.10. ESI-HRMS: Calcd. for [M+Na]$^+$: 391.39104. Found: 391.39139.

Example 13 to Example 15 are Reactions in which Hydroxyl is Converted to Iodide

Example 13

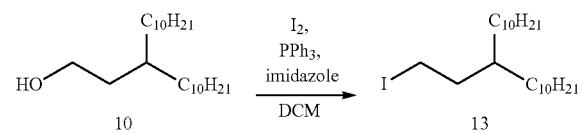

Scheme for Synthesizing Compound 13: Compound 10 (3.6 g, 10.6 mmol) was dissolved into dichloromethane, to which imidazole (0.93 g, 13.7 mmol) and triphenylphosphine (3.59 g 13.7 mmol) were added. Under ice bath, I$_2$ (3.48 g, 13.7 mmol) was added. After reacting under agitation at the room temperature for 4 h, Na$_2$SO$_3$ (aq.) was added for quenching. The organic phase was washed with saturated saline once and dried with anhydrous Na$_2$SO$_4$. After rotatory evaporation, it was loaded onto a silica gel column to obtain a colorless oily liquid Compound 13 with a yield of 95%. $^1$H NMR (CDCl$_3$, 400 MHz, ppm) δ: 3.21-3.17 (t, J=7.6 Hz, 2H), 1.83-1.77 (q, J=7.2 Hz, 2H), 1.40 (s, 1H), 1.33-1.24 (m, 37H), 0.90-0.86 (t, J=6.7 Hz, 6H). $^{13}$C NMR (CDCl$_3$, 100 MHz, ppm): δ 38.64, 38.28, 32.88, 31.93, 30.03, 29.69, 29.65, 29.36, 26.41, 22.70, 14.12, 5.15. EI-MS: Calcd. for [M-I]$^+$: 323. Found: m/z=323. Elemental Anal.: Calcd. for C$_{23}$H$_{47}$I: C, 61.32; H, 10.62. Found: C, 61.56; H, 10.60.

Example 14

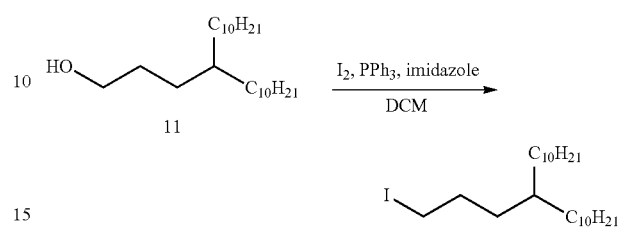

Scheme for Synthesizing Compound 14: Compound 11 was dissolved into dichloromethane, to which imidazole and triphenylphosphine were added. Under ice bath, I$_2$ was added. After reacting under agitation at the room temperature for 4 h, Na$_2$SO$_3$ (aq.) was added for quenching. The organic phase was washed with saturated saline once and dried with anhydrous Na$_2$SO$_4$. After rotatory evaporation, it was loaded onto a silica gel column to obtain a colorless oily liquid Compound 14 with a yield of 75%. $^1$H NMR (CDCl$_3$, 400 MHz, ppm) δ: 3.19-3.15 (t, J=7.0 Hz, 2H), 1.81-1.76 (p, J=7.1 Hz, 2H), 1.40-1.22 (m, 39H), 0.90-0.86 (t, J=6.8 Hz, 6H). $^{13}$C NMR (CDCl$_3$, 100 MHz, ppm) δ: 36.75, 34.60, 33.60, 31.93, 30.97, 30.08, 29.70, 29.66, 29.37, 26.66, 22.70, 14.11, 7.62. EI-MS: Calcd. for [M]$^+$: 464. Found: m/z=464. Calcd. for [M-I]$^+$: 337. Found: m/z=337. Elemental Anal.: Calcd. for C$_{24}$H$_{49}$I: C, 62.05; H, 10.63. Found: C, 62.35; H, 10.54.

Example 15

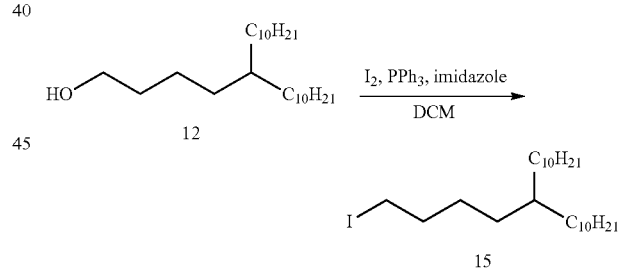

Scheme for Synthesizing Compound 15: Compound 12 was dissolved into dichloromethane, to which imidazole and triphenylphosphine were added. Under ice bath, I$_2$ was added. After reacting under agitation at the room temperature for 4 h, Na$_2$SO$_3$ (aq.) was added for quenching. The organic phase was washed with saturated saline once and dried with anhydrous Na$_2$SO$_4$. After rotatory evaporation, it was loaded onto a silica gel column to obtain a colorless oily liquid Compound 15 with a yield of 94%. $^1$H NMR (CDCl$_3$, 400 MHz, ppm) δ: 3.21-3.18 (t, J=7.0 Hz, 2H), 1.87-1.77 (p, J=7.1 Hz, 2H), 1.40-1.22 (m, 41H), 0.90-0.86 (t, J=6.8 Hz, 6H). $^{13}$C NMR (CDCl$_3$, 100 MHz, ppm): δ 37.25, 34.01, 33.59, 32.52, 31.94, 30.13, 29.71, 29.67, 29.37, 27.65, 26.67, 22.70, 14.12, 7.25. EI-MS: Calcd. for [M-I]$^+$: 351. Found: m/z=351. Elemental Anal.: Calcd. for C$_{25}$H$_{51}$I: C, 62.74; H, 10.74. Found: C, 62.87; II, 10.70.

Example 16

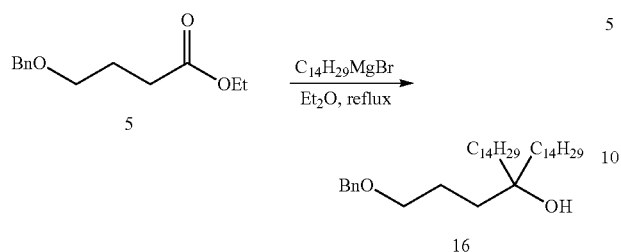

Scheme for Synthesizing Compound 16: Dry magnesium powders (3.0 g, 124 mmol) and an iodine grain were added into a three-necked bottle. Under nitrogen protection. 1-bromotetradecane (34.3 g, 124 mmol) in diethyl ether solution was added dropwise under room temperature. After the drop addition initiated the reaction, a one hour reflux was conducted. Then under an ice bath, the ether solution of Compound 5 (11 g, 49.5 mmol) was added dropwise into the system. After 5 h reflux, it was quenched with $H_2SO_4$ (2 M) under ice bath, and then extracted with diethyl ether (3×50 mL). After the organic phases were combined, it was washed with water and saturated saline. After dried with anhydrous $Na_2SO_4$ and rotatory evaporation, it was loaded onto the silica gel column for separation. 22.3 g of Compound 16 was obtained with a yield of 79%. $^1$H NMR (CDCl$_3$, 400 MHz, ppm): δ 7.36-7.25 (m, 5H), 4.51 (s, 2H), 3.50-3.47 (t, J=6.3 Hz, 2H), 2.98 (s, 1H), 1.69-1.62 (m, 2H), 1.52-1.49 (m, 2H), 1.43-1.39 (m, 4H), 1.32-1.26 (m, 48H), 0.90-0.86 (t, J=6.7 Hz, 6H). $^{13}$C NMR (CDCl$_3$, 100 MHz, ppm) δ: 138.40, 128.33, 127.58, 127.51, 73.95, 72.90, 70.99, 39.24, 36.11, 31.92, 30.29, 29.70, 29.68, 29.65, 29.36, 23.92, 23.54, 22.68, 14.11. ESI-HRMS: Calcd. for [M-OH]$^+$: 555.54994. Found: 555.55003.

Example 17

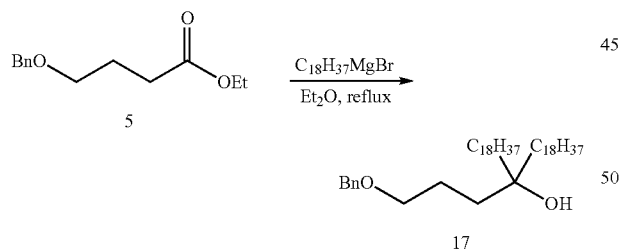

Scheme for Synthesizing Compound 17: Dry magnesium powders (2.72 g, 113 mmol) and an iodine grain were added into a three-necked bottle. Under nitrogen protection, 1-bromooctadecane (37.6 g, 113 mmol) in diethyl ether solution was added dropwise under room temperature. After the drop addition initiated the reaction, a one hour reflux was conducted. Then under an ice bath, the diethyl ether solution of Compound 5 (10 g, 45 mmol) was added dropwise into the system. After 5 h reflux, it was quenched with $H_2SO_4$ (2 M) under ice bath, and then extracted with diethyl ether (3×50 mL). After the organic phases were combined, it was washed with water and saturated saline. After dried with anhydrous $Na_2SO_4$ and rotatory evaporation, it was loaded onto the silica gel column for separation. 22.9 g of Compound 17 was obtained with a yield of 74%. $^1$H NMR (CDCl$_3$, 400 MHz, ppm): δ 7.34-7.26 (m, 5H), 4.51 (s, 2H), 3.50-3.47 (t, J=6.3 Hz, 2H), 1.66-1.63 (m, 2H), 1.52-1.48 (m, 2H), 1.43-1.39 (m, 4H), 1.32-1.21 (m, 64H), 0.90-0.86 (t. J=6.7 Hz, 6H). $^{13}$C NMR (CDCl$_3$, 100 MHz, ppm) δ: 138.39, 128.32, 127.56, 127.49, 73.92, 72.89, 70.98, 39.24, 36.11, 31.92, 30.29, 29.70, 29.69, 29.66, 29.36, 23.92, 23.54, 22.68, 14.10. ESI-HRMS: Calcd. for [M-OH]$^+$: 667.67514. Found: 667.67503.

Example 18

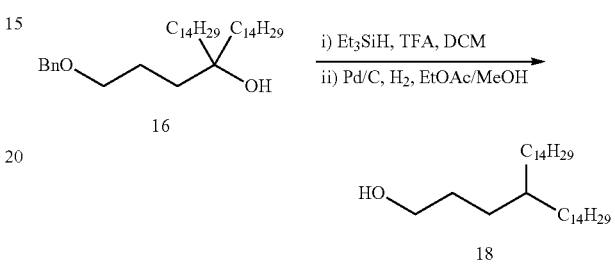

Scheme for Synthesizing Compound 18: Compound 16 (22 g, 38.4 mmol) was dissolved into 250 ml dry dichloromethane, to which Et$_3$SiH (5.3 g, 46.1 mmol) and TFA (21.9 g, 192 mmol) were added. After 12 h reaction under the room temperature, Na$_2$CO$_3$ (10 g) was added to quench the reaction until no bubble was generated. It was loaded onto a short silica gel column and eluted with dichloromethane, then a rotatory evaporation was conducted and followed by it was loaded onto a silica gel column for separation to obtain a colorless oily liquid. The resultant colorless oily liquid was dissolved into a mixed solvent of AcOEt/MeOH (300 mL/200 mL), to which 5% Pd/C (1 g) catalyst was carefully added. Then the reaction was conducted at the room temperature under one atmospheric pressure of hydrogen gas for 24h. It was loaded onto a flash column and eluted with ethyl acetate, then a rotatory evaporation was conducted and followed by it was loaded onto a silica gel column for separation. A white solid 18 was obtained with a yield of 68%. $^1$H NMR (CDCl$_3$, 400 MHz, ppm) δ: 3.64-3.61 (t, J=6.8 Hz, 2H), 1.58-1.50 (m, 2H), 1.32-1.23 (m, 55H), 0.90-0.86 (t, J=6.6 Hz, 6H). $^{13}$C NMR (CDCl$_3$, 100 MHz, ppm) 63.57, 37.24, 33.61, 31.93, 30.13, 29.99, 29.71, 29.67, 29.57, 29.37, 26.67, 22.69, 14.10.

Example 19

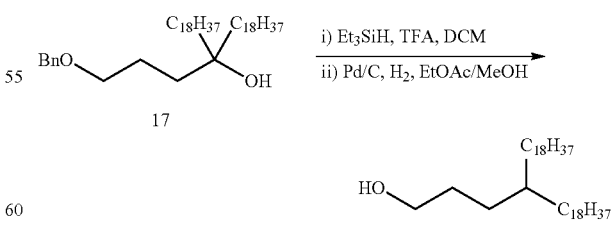

Scheme for Synthesizing Compound 19: Compound 17 (22.9 g, 33.4 mmol) was dissolved into 250 ml dry dichloromethane, to which Et$_3$SiH (4.66 g, 40.08 mmol) and TFA (19 g, 167 mmol) were added. After 12 h reaction under the room temperature, Na$_2$CO$_3$ (10 g) was added to quench the reaction until no bubble was generated. It was loaded onto a short silica gel column and eluted with dichloromethane, then a rotatory evaporation was conducted and followed by it was loaded onto a silica gel column for separation to obtain a colorless oily liquid. The resultant colorless oily liquid was dissolved into a mixed solvent of AcOEt/MeOH (300 mL/200 mL), to which 5% Pd/C (1 g) catalyst was carefully added. Then the reaction was conducted at the room temperature under one atmospheric pressure of hydrogen gas for 24h. It was loaded onto a flash column and eluted with ethyl acetate, then a rotatory evaporation was conducted and followed by it was loaded onto a silica gel column for separation. 12.9 g of white solid 19 was obtained with a yield of 67%. $^1$H NMR (CDCl$_3$, 400 MHz, ppm) δ: 3.63-3.60 (t, J=6.6 Hz, 2H), 1.57-1.51 (m, 2H), 1.32-1.24 (m, 71H), 0.90-0.86 (t, J=6.8 Hz, 6H). $^{13}$C NMR (CDCl$_3$, 100 MHz, ppm) δ: 63.52, 37.26, 33.62, 31.95, 30.16, 29.99, 29.74, 29.69, 29.59, 29.39, 26.69, 22.70, 14.10.

Example 20

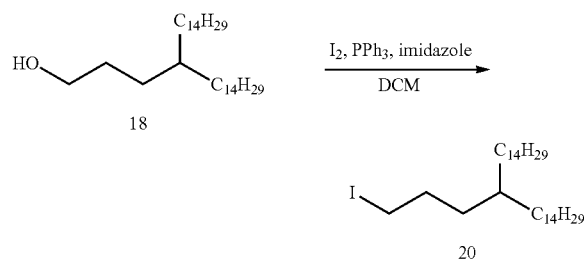

Scheme for Synthesizing Compound 20: Compound 18 (8.92 g, 19.1 mmol) was dissolved into dichloromethane, to which imidazole (1.56 g, 22.9 mmol) and triphenylphosphine (6.0 g, 22.9 mmol) were added. Under ice bath, I$_2$ (5.82 g, 22.9 mmol) was added. After reacting under agitation at the room temperature for 4 h, Na$_2$SO$_3$ (aq.) was added for quenching. The organic phase was washed with saturated saline once and dried with anhydrous Na$_2$SO$_4$. After rotatory evaporation, it was loaded onto a silica gel column to obtain 10.8 g of colorless oily liquid Compound 20 with a yield of 98%. $^1$H NMR (CDCl$_3$, 400 MHz, ppm) δ: 3.19-3.15 (t, J=7.0 Hz, 2H), 1.83-1.76 (m, 2H), 1.32-1.22 (m, 55H), 0.90-0.86 (t, J=6.6 Hz. 6H). EI-MS: Calcd. for [M]+: 576. Found: m/z=576.

Example 21

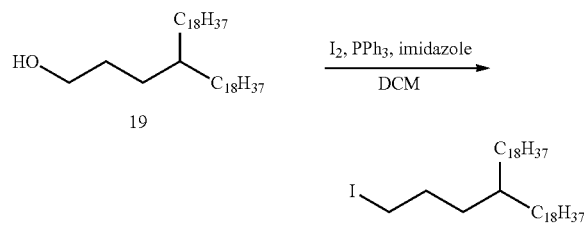

Scheme for Synthesizing Compound 21: Compound 19 (11.27 g, 19.46 mmol) was dissolved into dichloromethane, to which imidazole (1.59 g, 23.4 mmol) and triphenylphosphine (6.14 g, 23.4 mmol) were added. Under ice bath, I$_2$ (5.93 g, 23.4 mmol) was added. After reacting under agitation at the room temperature for 4 h, Na$_2$SO$_3$ (aq.) was added for quenching. The organic phase was washed with saturated saline once and dried with anhydrous Na$_2$SO$_4$. After rotatory evaporation, it was loaded onto a silica gel column to obtain 13.17 g of colorless oily liquid Compound 21 with a yield of 98%. $^1$H NMR (CDCl$_3$, 400 MHz, ppm) δ: 3.18-3.15 (t, J=7.0 Hz, 2H), 1.83-1.76 (p, J=7.1 Hz, 2H), 1.33-1.22 (m, 71H), 0.90-0.86 (t, J=6.6 Hz, 6H). $^{13}$C NMR (CDCl$_3$, 100 MHz, ppm) δ: 36.75, 34.60, 33.61, 31.96, 30.97, 30.10, 29.74, 29.72, 29.70, 29.40, 26.67, 22.72, 14.13, 7.55. EI-MS: Calcd. for [M]+: 688. Found: m/z=688.

Example 22

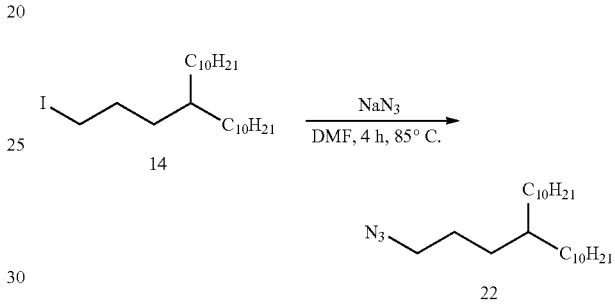

Scheme for Synthesizing Compound 22: Compound 14 (1.0 g, 2.15 mmol) was dissolved into 100 ml DMF. At the room temperature, sodium azide (0.7 g, 10.5 mmol) was added in batches. After reaction under agitation at 85° C. for 4h, DMF was removed by vacuum distillation. Extraction was conducted with petroleum ether. The organic phase was washed with saturated saline once and dried with anhydrous Na$_2$SO$_4$. The solvent was removed by vacuum to obtain the product 22 (0.81 g) with a yield of 100%. $^1$H NMR (CDCl$_3$, 400 MHz, ppm) δ: 3.26-3.22 (t, J=7.0 Hz, 2H), 1.81-1.76 (p, J=7.1 Hz, 2H), 1.40-1.22 (m, 39H), 0.90-0.86 (t, J=6.8 Hz, 6H). EI-MS: Calcd. for [M]+: 379. Found: m/z=379.

Example 23

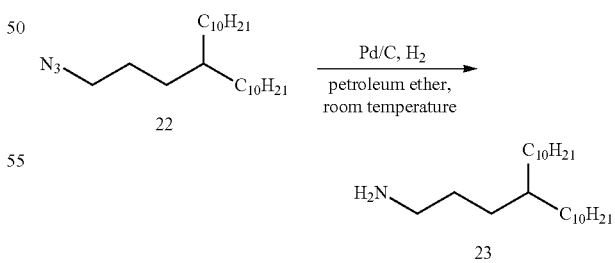

Scheme for Synthesizing Compound 23: Compound 22 (0.81 g, 2.15 mmol) was dissolved in 100 ml petroleum ether. Pd/C (0.1 g) was added. At the room temperature, hydrogenation was conducted for 12 h, followed by filtration with kieselguhr and column separation to obtain 0.6 g of colorless oily liquid Compound 23 with a yield of 80%. $^1$H NMR (CDCl$_3$, 400 MHz, ppm) δ: 3.26-3.22 (t, J=7.0 Hz, 2H), 1.81-1.76 (p, J=7.1 Hz, 2H), 1.40-1.22 (m, 39H), 0.90-0.86 (t, J=6.8 Hz, 6H). EI-MS: Calcd. for [M]+: 354. Found: m/z=354.

Example 24 to Example 28 are Reactions for Preparing the Monomers for Polymerization Example 24

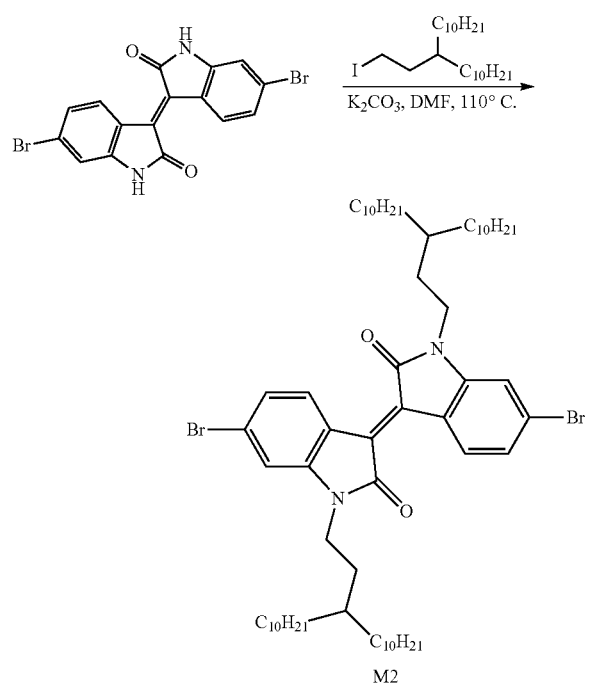

M2

Synthesis of Monomer M2: 6,6'-dibromoisoindigo (1.70 g, 4.04 mmol) and potassium carbonate (1.68 g, 12.1 mmol) were dissolved in DMF (100 mL). Compound 13 (4.19 g, 9.31 mmol) was added under nitrogen protection. Reaction was conducted under agitation at temperature of 110° C. for 15 h. After the complete of the reaction, the solvent was removed by rotatory evaporation. After solvation into CHCl$_3$ (100 mL) and washed with water for three times, the organic phases were combined and washed with saturated saline once, and then dried with anhydrous Na$_2$SO$_4$. After rotatory evaporation, it was loaded onto a silica gel column for separation to obtain 3.79 g of dark red solid M2 with a yield of 88%. $^1$H NMR (CDCl$_3$, 400 MHz, ppm) δ: 9.09-9.07 (d, 8.6 Hz, 2H), 7.17-7.15 (dd. J=8.6 Hz, J$_2$=1.6 Hz, 2H), 6.89-6.88 (d, J=1.6 Hz, 2H), 3.74-3.70 (t, J=7.4 Hz 4H), 1.71-1.56 (q, J=6.3 Hz, 4H), 1.42-1.26 (m, 74H), 0.90-0.86 (t, J=6.8 Hz, 4H). $^{13}$C NMR (CDCl$_3$, 100 MHz, ppm): δ 167.49, 145.68, 132.55, 131.22, 126.66, 125.05, 120.44, 111.18, 55 38.39, 35.61, 33.44, 31.93, 30.96, 30.04, 29.70, 29.69, 29.66, 29.36, 26.62, 22.70, 14.12. Elemental Anal.: Calcd. for C$_{62}$H$_{100}$Br$_2$N$_2$O$_2$: C, 69.90; H, 9.46; N, 2.63. Found: C, 69.78; H, 9.46; N, 2.62. ESI-HRMS: Calcd. for [M+H]$^+$: 1063.62243. Found: 1063.62480.

Example 25

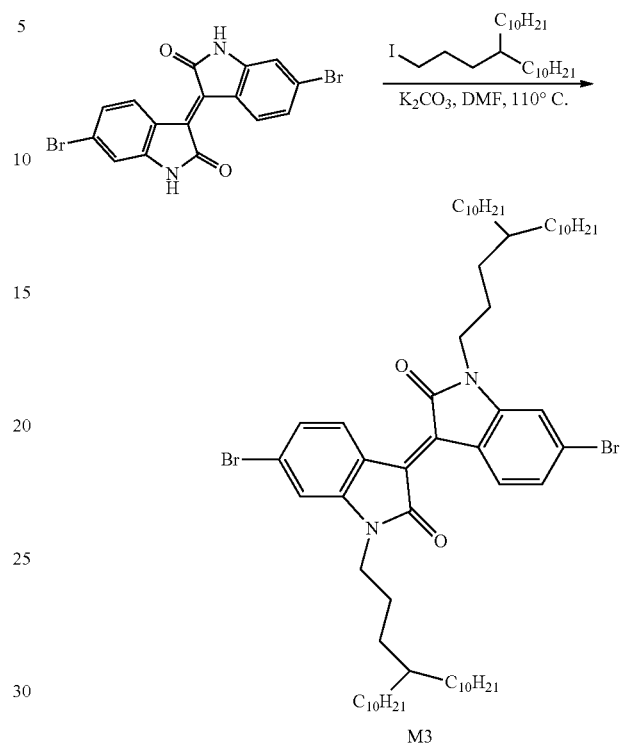

M3

Synthesis of Monomer M3: 6,6'-dibromoisoindigo and potassium carbonate were dissolved in DMF (100 mL). Compound 14 was added under nitrogen protection. Reaction was conducted under agitation at temperature of 110° C. for 15 h. After the complete of the reaction, the solvent was removed by rotatory evaporation. After dissolved into CHCl$_3$ (100 mL) and washed with water for three times, the organic phases were combined and washed with saturated saline once, and then dried with anhydrous Na$_2$SO$_4$. After rotatory evaporation, it was loaded onto a silica gel column for separation to obtain a dark red solid M3 with a yield of 71%. $^1$H NMR (CDCl$_3$, 400 MHz, ppm) δ: 9.10-9.08 (d, J=8.6 Hz, 2H), 7.18-7.16 (dd, J$_1$=8.6 Hz, J$_2$=1.6 Hz, 2H), 6.93-6.92 (d, J=1.6 Hz, 2H), 3.73-3.69 (t, J=7.4 Hz, 4H), 1.68-1.64 (m, 4H), 1.34-1.22 (m, 78H), 0.89-0.86 (t, J=6.6 Hz, 12H). $^{13}$C NMR (CDCl$_3$, 100 MHz, ppm): δ 167.68, 145.76, 132.60, 131.21, 126.72, 125.10, 120.41, 111.28, 40.61, 37.10, 33.52, 31.93, 30.81, 30.09, 29.69, 29.65, 29.36, 26.67, 24.47, 22.69, 14.12. Elemental Anal.: Calcd. for C$_{64}$H$_{104}$Br$_2$N$_2$O$_2$: C, 70.31; H, 9.59; N, 2.56. Found: C, 70.50; H, 9.62; N, 2.53. ESI-HRMS: Calcd. for [M+H]$^+$: 1091.65373. Found: 1093.65487.

Example 26

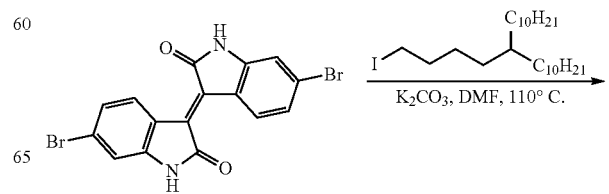

-continued

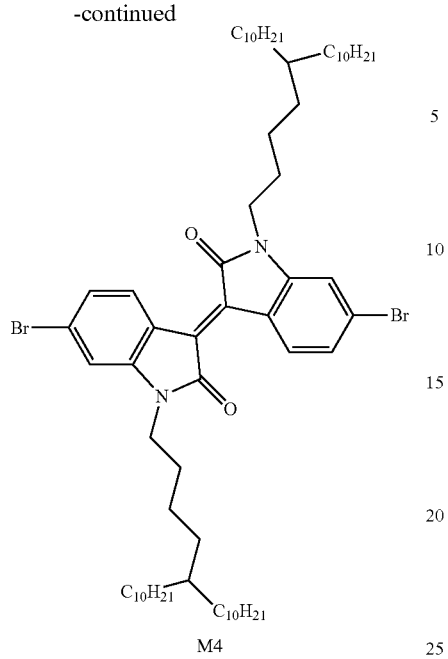

M4

-continued

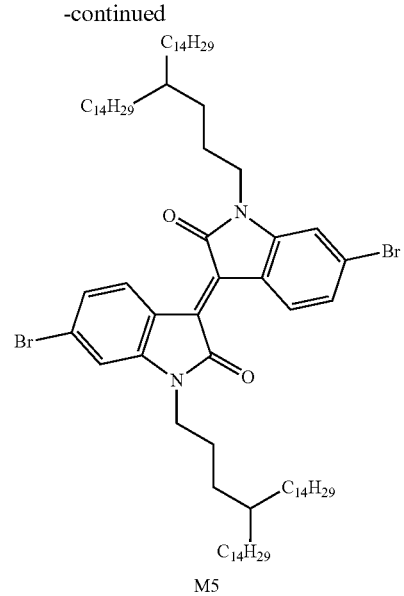

M5

Synthesis of Monomer M4: 6,6'-dibromoisoindigo and potassium carbonate were dissolved in DMF (100 mL). Compound 15 was added under nitrogen protection. Reaction was conducted under agitation at temperature of 110° C. for 15 h. After the complete of the reaction, the solvent was removed by rotatory evaporation. After dissolved into CHCl$_3$ (100 mL) and washed with water for three times, the organic phases were combined and washed with saturated saline once, and then dried with anhydrous Na$_2$SO$_4$. After rotatory evaporation, it was loaded onto a silica gel column for separation to obtain a dark red solid M4 with a yield of 83%. $^1$H NMR (CDCl$_3$, 400 MHz, ppm) δ: 9.10-9.07 (d, J=8.6 Hz, 2H), 7.17-7.14 (dd, J$_1$=8.6 Hz, J$_2$=1.6 Hz, 2H), 6.92-6.91 (d, J=1.6 Hz, 2H), 3.74-3.70 (t, J=7.4 Hz, 4H), 1.67-1.62 (m, 4H), 1.36-1.22 (m, 82H), 0.89-0.86 (t, J=6.8 Hz, 12H). $^{13}$C NMR (CDCl$_3$, 100 MHz, ppm): δ 167.67, 145.76, 132.59, 131.23, 126.71, 125.10, 120.41, 111.26, 40.27, 37.39, 33.61, 33.36, 31.93, 30.13, 29.72, 29.66, 29.37, 27.78, 26.71, 24.22, 22.70, 14.12. Elemental Anal.: Calcd. for C$_{66}$H$_{108}$Br$_2$N$_2$O$_2$: C, 70.69; H, 9.71; N, 2.50. Found: C, 70.79; H, 9.55; N, 2.49. ESI-HRMS: Calcd. for [M+Na]$^+$: 1141.66698. Found: 1141.66836.

Synthesis of Monomer M5: 6,6'-dibromoisoindigo (2 g, 4.76 mmol) and potassium carbonate (1.97 g, 14.28 mmol) were dissolved in DMF (100 mL). Compound 20 (6.0 g, 10.4 mmol) was added under nitrogen protection. Reaction was conducted under agitation at temperature of 100° C. for 15 h. After the complete of the reaction, the solvent was removed by rotatory evaporation. After dissolved into CHCl$_3$ (100 mL) and washed with water for three times, the organic phases were combined and washed with saturated saline once, and then dried with anhydrous Na$_2$SO$_4$. After rotatory evaporation, it was loaded onto a silica gel column for separation to obtain 6.0 g of dark red solid M5 with a yield of 95%. $^1$H NMR (CDCl$_3$, 400 MHz, ppm) δ: 9.10-9.08 (d, J=8.6 Hz, 2H), 7.18-7.15 (dd, J$_1$=8.6 Hz, J$_2$=1.8 Hz, 2H), 6.93-6.92 (d, J=1.8 Hz, 2H), 3.73-3.69 (t, J=7.5 Hz, 4H), 1.67-1.64 (m, 4H), 1.34-1.22 (m. 114H), 0.89-0.86 (t, J=6.6 Hz, 12H).

Example 27

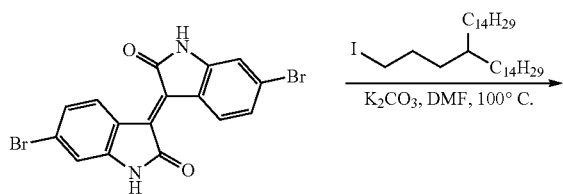

Example 28

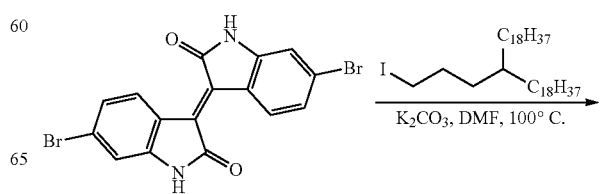

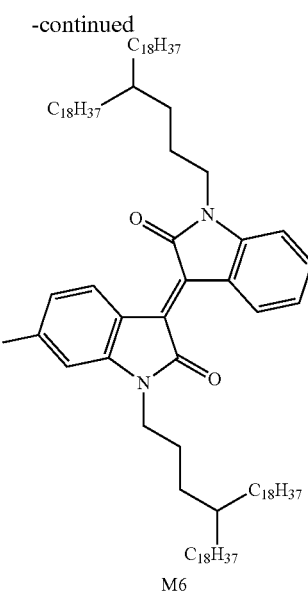

M6

Synthesis of Monomer M6: 6,6'-dibromoisoindigo (1.5 g, 3.57 mmol) and potassium carbonate (1.48 g, 10.71 mmol) were dissolved in DMF (100 mL). Compound 21 (5.41 g, 7.86 mmol) was added under nitrogen protection. Reaction was conducted under agitation at temperature of 100° C. for 15 h. After the complete of the reaction, the solvent was removed by rotatory evaporation. After dissolved into $CHCl_3$ (100 mL) and washed with water for three times, the organic phases were combined and washed with saturated saline once, and then dried with anhydrous $Na_2SO_4$. After rotatory evaporation, it was loaded onto a silica gel column for separation to obtain 4.95 g of dark red solid M6 with a yield of 90%. $^1$H NMR ($CDCl_3$, 400 MHz, ppm) $^1$H NMR ($CDCl_3$, 400 MHz, ppm) δ: 9.10-9.08 (d, J=8.6 Hz, 2H), 7.18-7.15 (dd, $J_1$=8.6 Hz, $J_2$=1.8 Hz, 2H), 6.93-6.92 (d, J=1.8 Hz, 2H), 3.73-3.69 (t, J=7.5 Hz, 4H), 1.67-1.64 (m, 4H), 1.34-1.22 (m, 142H), 0.89-0.86 (t, J=6.6 Hz, 12H).

Example 29 to Example 31 are Polymerization for the Polymers

Example 29

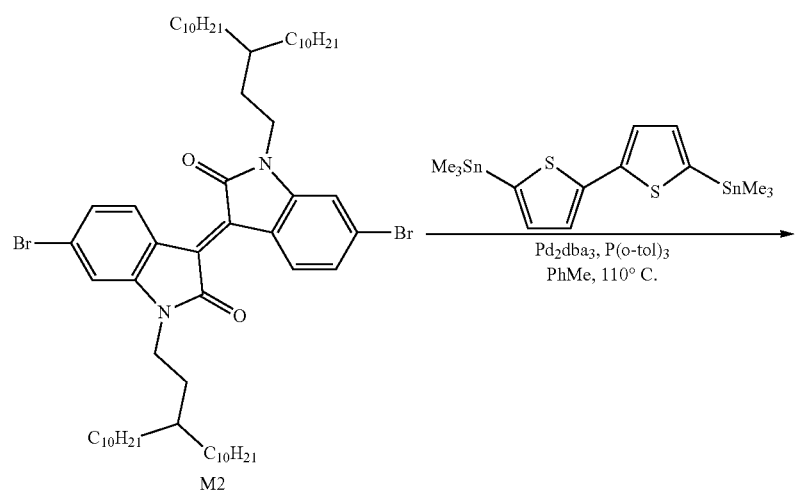

M2

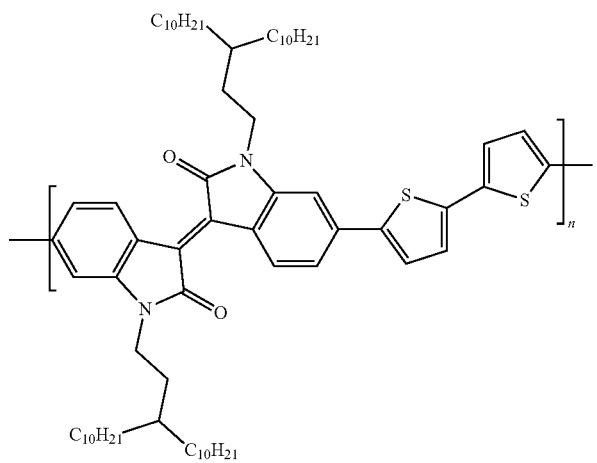

P2

Synthesis of Polymer P2: Under nitrogen protection. M2 (0.235 mmol), 5,5'-bis(trimethylstannyl)-2,2'-bithiophene (0.235 mmol), Pd$_2$(dba)$_3$ (4.3 mg, 2 mol %), P(o-tol)$_3$ (5.7 mg, 8 mol %), and 10 ml dry toluene solvent were added into a reaction flask. After reaction with agitation at temperature of 110° C. for 24 h, Soxhlet extraction was conducted with chloroform to obtain the product (236 mg, with a yield of 95%). Elemental Anal. Calcd: for $(C_{70}H_{104}N_2O_2S_2)_n$: C, 78.52; H, 9.88; N, 2.62. Found: C, 77.78; H, 9.47; N, 2.55.

Synthesis of Polymer P3: Under nitrogen protection, M3 (0.229 mmol), 5,5'-bis(trimethylstannyl)-2,2'-bithiophene (0.229 mmol), Pd$_2$(dba)$_3$ (4.3 mg, 2 mol %), P(o-tol)$_3$ (5.6 mg, 8 mol %), and 10 ml dry toluene solvent were added into a reaction flask. After reaction with agitation at temperature of 110° C. for 24 h, Soxhlet extraction was conducted with chloroform to obtain the product (238 mg, with a yield of 94%). Elemental Anal.: Calcd. for $(C_{72}H_{108}N_2O_2S_2)_n$: C, 77.78; H, 9.92; N, 2.55. Found: C, 77.85; H, 9.75; N, 2.48.

Example 30

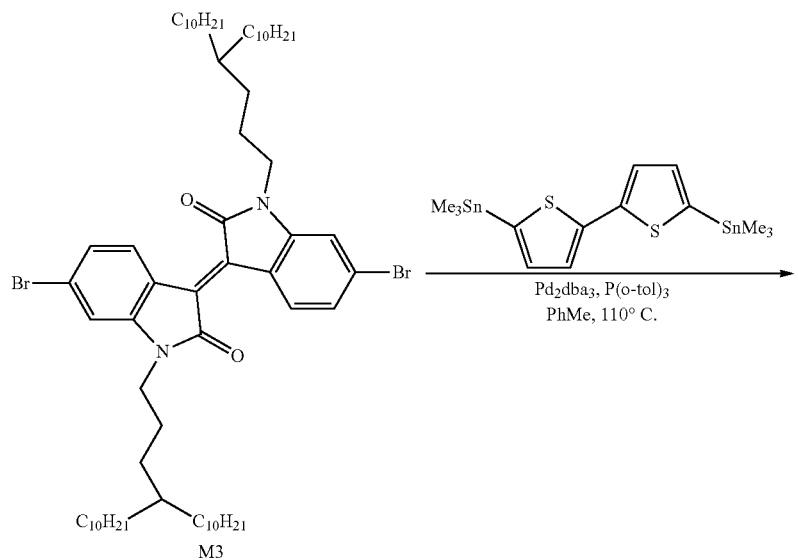

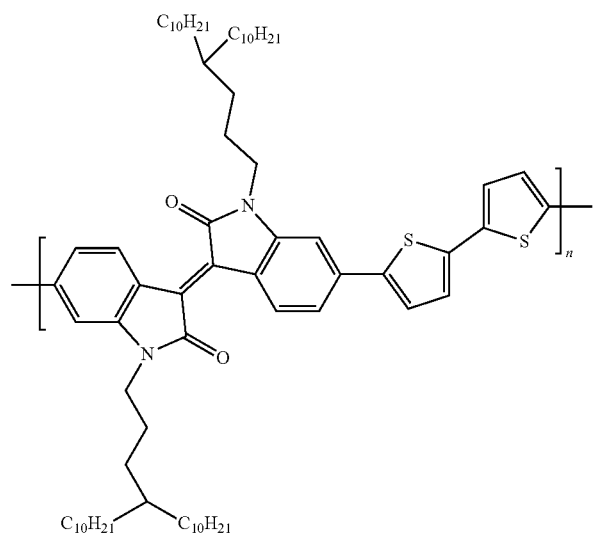

Example 31

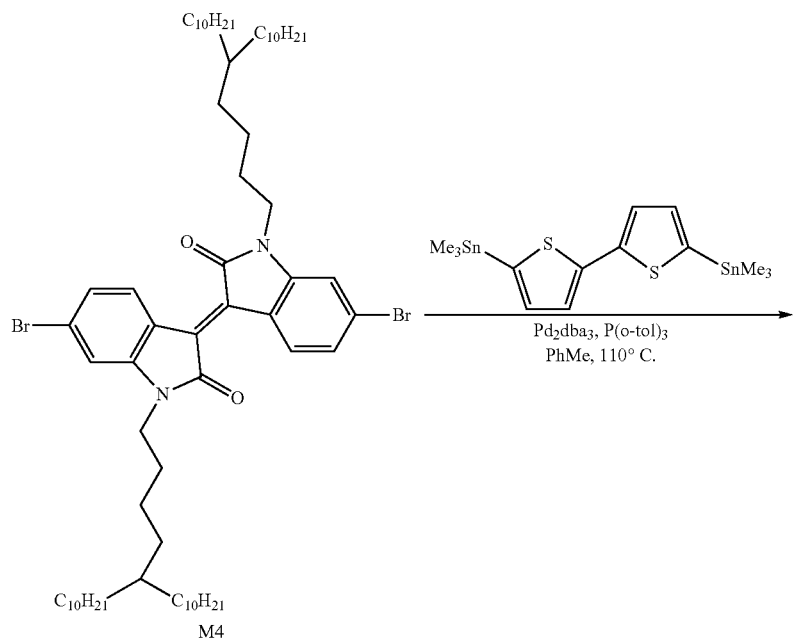

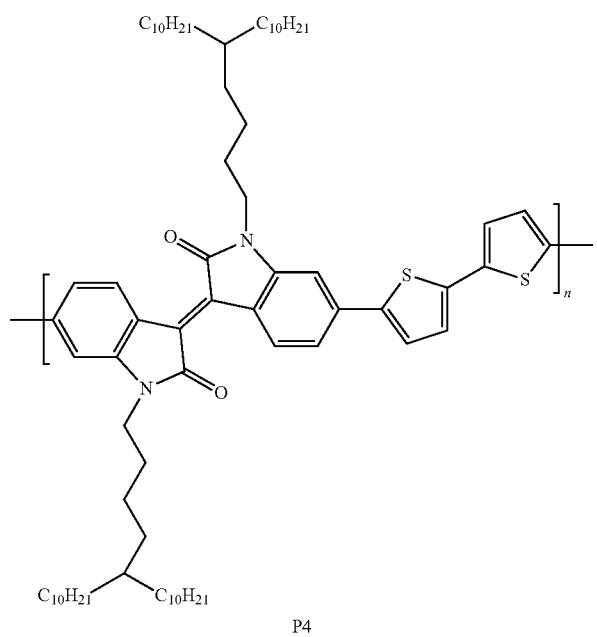

Synthesis of Polymer P4: Under nitrogen protection, M4 (0.229 mmol), 5,5'-bis(trimethylstannyl)-2,2'-bithiophene (0.229 mmol), $Pd_2(dba)_3$ (4.2 mg, 2 mol %), $P(o\text{-tol})_3$ (5.6 mg, 8 mol %), and 10 ml dry toluene solvent were added into a reaction flask. After reaction with agitation at temperature of 110° C. for 24 h, Soxhlet extraction was conducted with chloroform to obtain the product (220 mg, with a yield of 87%). Elemental Anal.: Calcd. for $(C_{74}H_{112}N_2O_2S_2)_n$: C, 78.95; H, 10.03; N, 2.49. Found: C, 78.25; H, 9.91; N, 2.46.

Example 32

The optical physical properties and electrochemical properties of Polymers P2, P3, and P4 were characterized and the data are shown in the following table:

TABLE 1

The optical physical and electrochemical properties of Polymers P1-P4

| Polymer | Molecular Weight $M_n$ (kDa)/PDI | Decomposition Temperature (° C.) | $\lambda_{max}$ sol. (nm)[a] | $\lambda_{max}$ film (nm)[b] | $E_g^{opt}$ (eV)[c] | $E_{HOMO}$ (eV)[d] | $E_{LUMO}$ (eV)[d] | $E_g^{cv}$ (eV)[e] | $E_{HOMO\ PES}$ (eV)[f] |
|---|---|---|---|---|---|---|---|---|---|
| P1 | 20.4/2.0 | 390 | 706, 647 | 701, 637 | 1.60 | −5.70 | −3.70 | 2.00 | −5.54 |
| P2 | 18.4/2.0 | 384 | 711, 647 | 707, 641 | 1.60 | −5.60 | −3.70 | 1.90 | −5.57 |
| P3 | 39.2/3.2 | 392 | 718, 673 | 719, 653 | 1.58 | −5.52 | −3.74 | 1.78 | −5.33 |
| P4 | 37.3/2.3 | 374 | 719, 675 | 716, 647 | 1.58 | −5.50 | −3.74 | 1.76 | −5.26 |

[a]Longest absorption wavelength of the solution (corresponding to 0-0 vibration absorption and 0-1 vibration absorption, respectively);
[b]longest absorption wavelength of the film (corresponding to 0-0 vibration absorption and 0-1 vibration absorption, respectively);
[c]band gap in the absorption spectrum;
[d]electrochemical measurement value;
[e]electrochemical band gap;
[f]photoelectron spectrum (PES) measurement value.

Among them, P1 is a 2-branching polymer (Lei, T.; Cao, Y.; Fan, Y.; Liu, C. J.; Yuan, S. C.; Pei, J. J. Am. Chem. Soc. 2011, 133, 6099), whose structure is as follows:

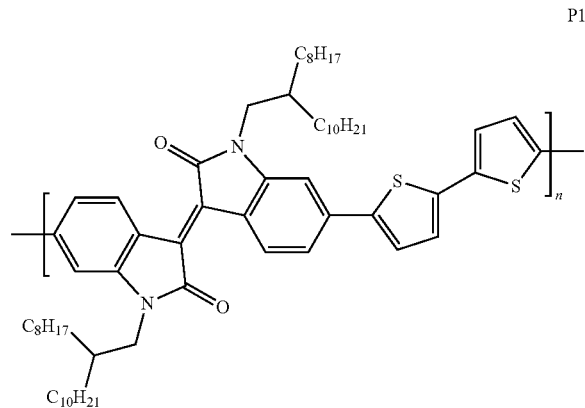

P1

P2~P4 are polymers synthesized in the invention. After the introduction of different branching alkyl chains, significant change occurred to the spectra and electrochemistry of P2~P4. The absorption spectra apparently shifted to red, the HOMO energy levels apparently increased, and the band gaps apparently reduced. These changes were due to the changes of the mode of stacking between polymers.

Example 33

Device Processing and X-Ray Diffraction Characterization of the Organic Field Effect Transistor Comprising Polymers P1-P4

Processing of the organic field effect transistor (OTFT) was conducted with the device structure of bottom-gate/top-contact (BG/TC). For the substrate, doped silicon ($n^{++}$-Si) was used as a gate electrode, and 300 nm silicon dioxide was used as an insulation layer. The substrate was washed with acetone, a detergent, water and isopropanol successively before dried with nitrogen blow. Then the substrate was cleaned with plasma beam for 15 minutes, and modified with octadecylsilane. Then the dichlorobenzene solution of the polymer was spin coated onto the substrate and annealed at different temperatures. Then at high vacuum, a layer of 30 mm gold electrode was coated by hot vapor deposition with a physical mask as the source electrode and the drain electrode. The measurement of the mobility of the polymer was conducted on a Keithley 4200 semiconductor characterization system.

The experiments proved that compared to P1, the mobility of P3 had great increase from the initial 0.79 $cm^2V^{-1}s^{-1}$ (P1) to 3.62 $cm^2V^{-1}s^{-1}$. The threshold voltage also significantly decreased.

The X ray diffraction experiment was conducted on Beamline BL14B1 at Shanghai Synchrotron Radiation Facility with a wavelength of 1.2398 Å, and the measurement was conducted with an NaI counter. The experiments proved that the type of branching alkyl chains contained in the polymers effectively reduced the π-π stacking distance between polymers. This result also proved the huge effect of the novel alkyl chain of the disclosure in organic semiconductor devices.

TABLE 2

Performance of the organic field effect transistors and results of the film glancing X-ray study

| Polymer | Annealing Temperature (° C.) | Mobility ($cm^2V^{-1}s^{-1}$)[a] | Threshold Voltage (V) | on/off ratio $I_{on}/I_{off}$ | d(Å)[b] L | d(Å)[b] π |
|---|---|---|---|---|---|---|
| P1 | 150 | 0.79 (0.45) | −18 | >$10^6$ | 20.3 | 3.75 |
| P2 | 200 | 0.40 (0.28) | −10 | >$10^5$ | 23.7 | 3.61 |
| P3 | 175 | 3.62 (2.98) | −2 | >$10^6$ | 24.7 | 3.57 |
| P4 | 175 | 1.76 (1.44) | −5 | >$10^6$ | 26.1 | 3.57 |

[a]The measurement was conducted in air (RH = 50~60%). Maximal mobility values were shown outside the parentheses, while average values were shown in the parentheses.
[b]The layer phase distance (L) and π-π stacking distance (π) obtained in the X-ray study.

The invention claimed is:
1. A Formula (II) polymer:

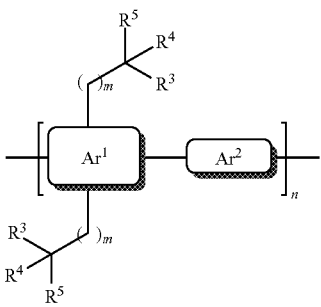

Formula (II)

wherein $Ar^1$ and $Ar^2$ represent different aromatic compound fragments; n is an integer which represents the polymerization degree of the polymer; m is an integer of from 3 to 18; $R^3$ and $R^4$ are the same or different, independently selected from alkyl, halogen substituted alkyl, alkoxy, halogen substituted alkoxy, alkenyl and alkynyl; and $R^5$ is hydrogen, hydroxyl, alkyl, halogen substituted alkyl, alkoxy, halogen substituted alkoxy, alkenyl or alkynyl.

2. The Formula (II) polymer according to claim 1, wherein the polymer is obtained by polymerization of the aromatic compound monomers with the structures as shown in anyone of the following Formulae III -1 to III -16

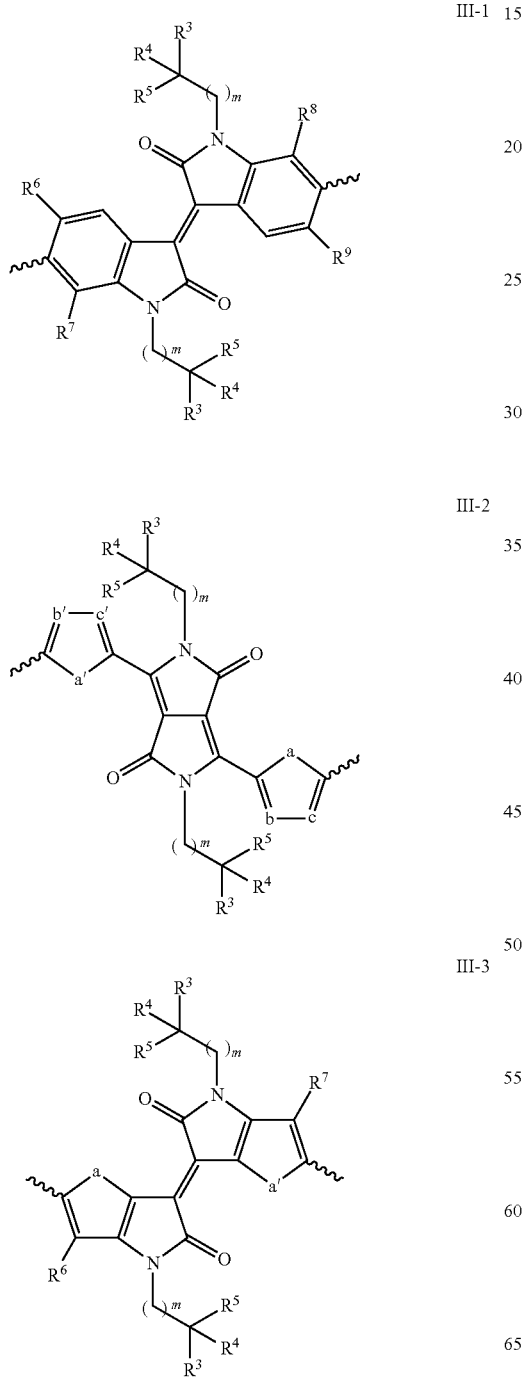

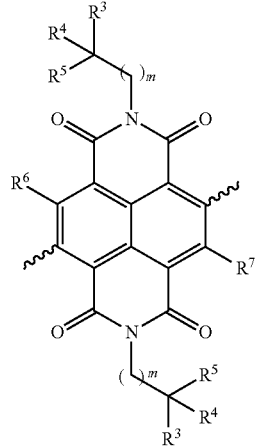

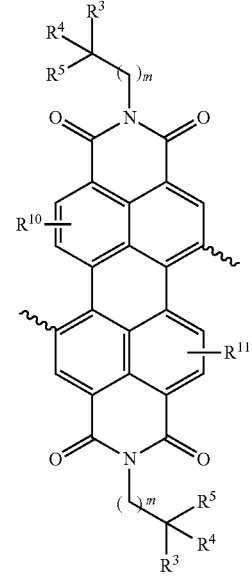

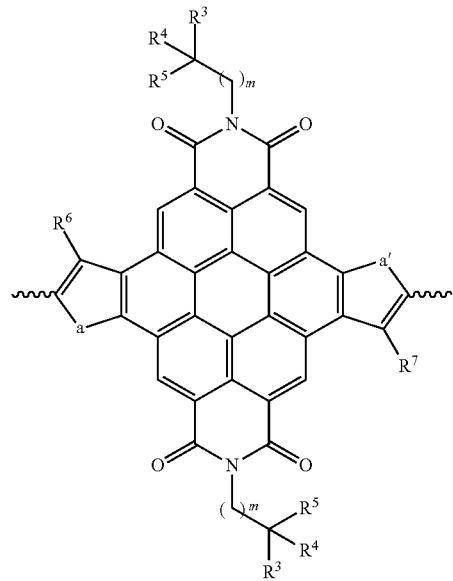

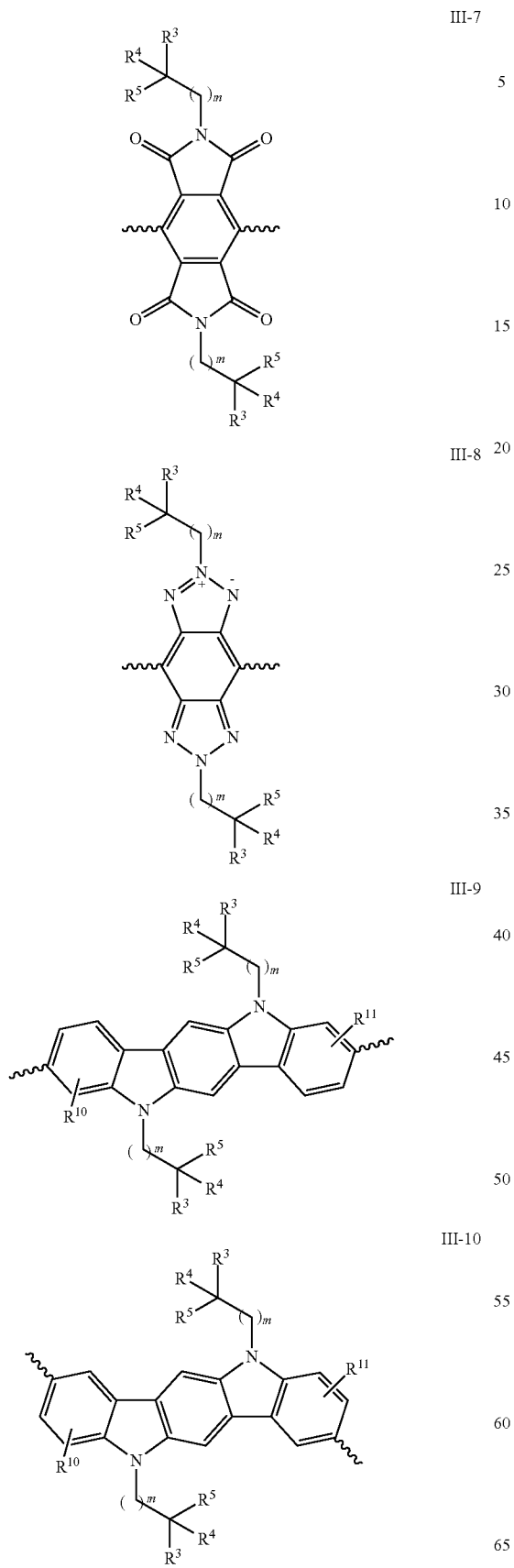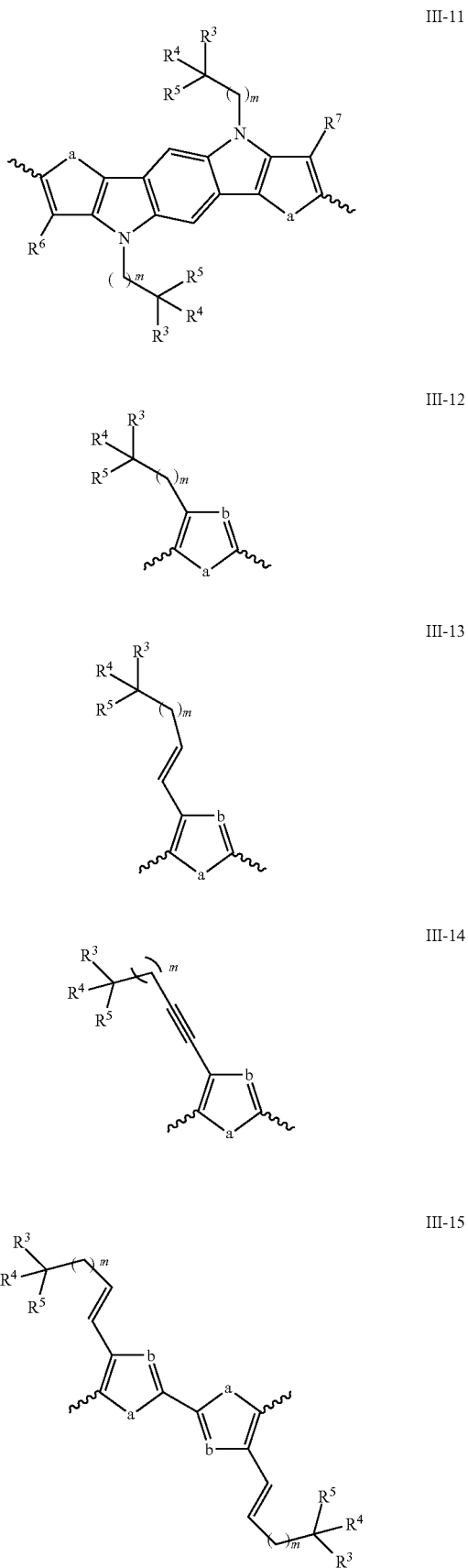

-continued

III-16

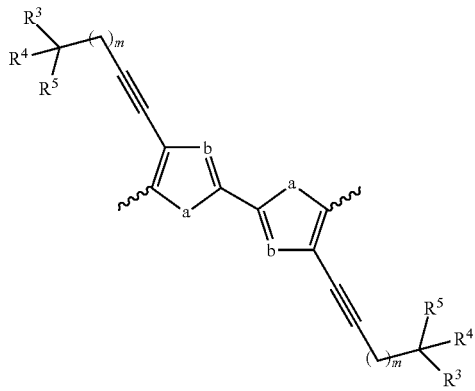

wherein in the aforementioned Formulae III-1 to III-16, $R^6$, $R^7$, $R^8$ and $R^9$ represent substituents on the aromatic ring, independently selected from hydrogen atom, halogen atom, nitro, amino, cyano, alkyl, alkenyl, alkynyl, alkoxy, halogen substituted alkyl and halogen substituted alkoxy; $R^{10}$ and $R^{11}$ represents one or more substituents on the aromatic ring which are independently selected from hydrogen atom, halogen atom, nitro, amino, cyano, alkyl, alkenyl, alkynyl, alkoxy, halogen substituted alkyl and halogen substituted alkoxy; a and a' are independently selected from the following structures: —S—, —O—, —Se—, and —NR$^{12}$—; b, b', c and c' are independently selected from the following structures: —N=, =N—, —CR$^{12}$=, and =CR$^{12}$—, wherein R$^{12}$ represents hydrogen atom, alkyl, alkenyl, alkynyl, alkoxy, halogen substituted alkyl, halogen substituted alkoxy, aryl or heteroaryl; and the Ar$^2$ aromatic compound monomer.

3. A photoelectric device comprising the Formula (II) polymer of claim 1 as organic semiconductor materials.

4. The photoelectric device of claim 3, which is an organic solar cell, an organic light emitting diode or an organic field effect transistor.

* * * * *